United States Patent
Wirt et al.

(10) Patent No.: US 6,458,095 B1
(45) Date of Patent: Oct. 1, 2002

(54) DISPENSER FOR AN ADHESIVE TISSUE SEALANT HAVING A HOUSING WITH MULTIPLE CAVITIES

(75) Inventors: David F. Wirt, El Granada, CA (US); Larry H. Dodge, River Falls, WI (US); Jeffrey D. Smith, Marine On St. Croix, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/524,141

(22) Filed: Mar. 10, 2000

Related U.S. Application Data

(63) Continuation-in-part of application No. 08/956,308, filed on Oct. 22, 1997.

(51) Int. Cl.[7] .............................................. A61M 37/00

(52) U.S. Cl. ........................ 604/82; 604/86; 604/191; 222/137

(58) Field of Search .............................. 604/82–86, 89, 604/90, 191, 208, 500, 506, 508, 522; 222/137, 145.1, 145.3, 145.4

(56) References Cited

U.S. PATENT DOCUMENTS

| | | |
|---|---|---|
| 1,612,116 A | 12/1926 | Heublein |
| 3,767,085 A | 10/1973 | Cannon et al. ............... 222/82 |
| 4,141,973 A | 2/1979 | Balazs ........................ 424/180 |
| 4,359,049 A | 11/1982 | Redl et al. |
| 4,599,082 A | 7/1986 | Grimard ...................... 604/90 |
| 4,631,055 A | 12/1986 | Redl et al. .................... 604/82 |
| 4,735,616 A | 4/1988 | Eibl et al. .................... 604/191 |
| 4,861,335 A | 8/1989 | Reynolds ..................... 604/88 |
| 4,874,368 A | 10/1989 | Miller et al. ................. 604/82 |

(List continued on next page.)

FOREIGN PATENT DOCUMENTS

| | | |
|---|---|---|
| EP | 0 298 585 | 1/1989 |
| EP | 0 292 472 | 10/1991 |
| EP | 0 634 140 | 1/1995 |
| WO | WO 99/17833 | 4/1999 |
| WO | WO 99/20328 | 4/1999 |
| WO | WO 99/32155 | 7/1999 |
| WO | WO 99/32173 | 7/1999 |

OTHER PUBLICATIONS

Healon® Brochure (undated).
Tisseel® VH Fibrin Sealant Brochure (dated 1998) from Baxter (4 pages) and Tisseel® VH and Fibrin Sealant Kit Quick Reference Guide (dated 1998) (2 pages).
Product Insert Tisseel® VH Kit Two Component Fibrin Sealant, Vapor Heated Kit from Immuno, distributed by Baxter Healthcare (4 pages) (1998).
Informal English Translation of Beriplast® Fibrin Adhesive Set from Behring dated 1991 (4 pages).

*Primary Examiner*—Gregory Huson
*Assistant Examiner*—Tuan Nguyen
(74) *Attorney, Agent, or Firm*—John A. Burtis

(57) ABSTRACT

A dispenser in which a dry powder (one component of a two-part adhesive tissue sealant and/or adhesive) is stored in a container (e.g., a carpule) having a septum at one end, an open end opposite the septum, and a movable plug. The powder is retained at the septum end of the container by the movable plug, which is displaced and pushed back as the solvent used for reconstituting the powder is introduced (e.g., through the septum). The second part of the tissue sealant is contained within a second container, also with a movable plug. After the first part is reconstituted, a manifold is fitted which pierces both septums and allows the contents to be dispensed. A dual syringe body supports the containers, and has pistons that enter the open ends to advance the movable plugs. Other embodiments of tissue adhesive and/or sealant dispensers and kits as well as methods of preparing tissue sealants are also described.

30 Claims, 15 Drawing Sheets

U.S. PATENT DOCUMENTS

| | | |
|---|---|---|
| 4,886,495 A | 12/1989 | Reynolds .................... 604/88 |
| 4,978,336 A | 12/1990 | Capozzi et al. ............... 604/82 |
| 5,080,493 A | 1/1992 | McKown et al. ........... 366/177 |
| 5,185,001 A | 2/1993 | Galanakis |
| 5,314,412 A | 5/1994 | Rex ........................... 604/191 |
| 5,324,775 A | 6/1994 | Rhee et al. ................ 525/54.2 |
| 5,386,928 A | 2/1995 | Blette ......................... 222/94 |
| 5,464,396 A | 11/1995 | Barta et al. ................ 604/191 |
| 5,474,540 A | 12/1995 | Miller et al. ................ 604/191 |
| 5,489,266 A | 2/1996 | Grimard ...................... 604/89 |
| 5,514,379 A | 5/1996 | Weissleder et al. ......... 424/426 |
| 5,527,856 A | 6/1996 | Rhee et al. ................ 525/54.1 |
| 5,542,934 A | 8/1996 | Silver ........................ 604/191 |
| 5,550,187 A | 8/1996 | Rhee et al. ................ 525/54.1 |
| 5,582,596 A | 12/1996 | Fukunaga et al. ........... 604/191 |
| 5,583,114 A | 12/1996 | Barrows et al. ............... 514/21 |
| 5,928,611 A | 7/1999 | Leung ....................... 422/131 |

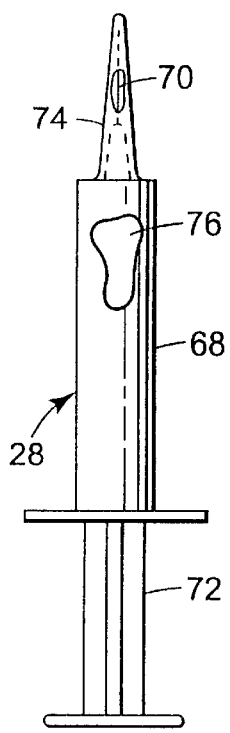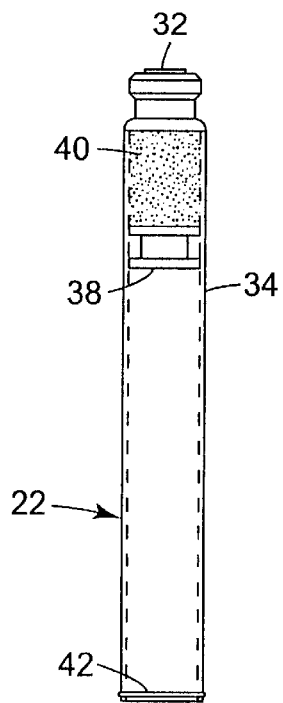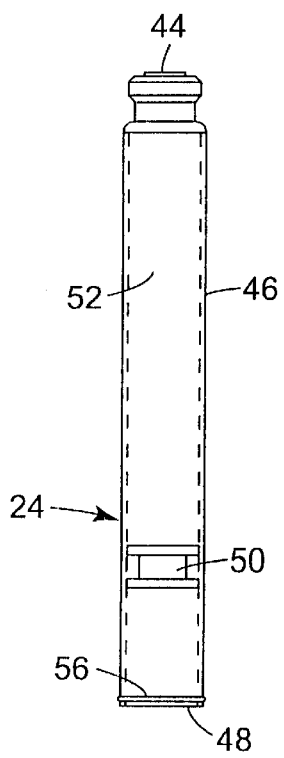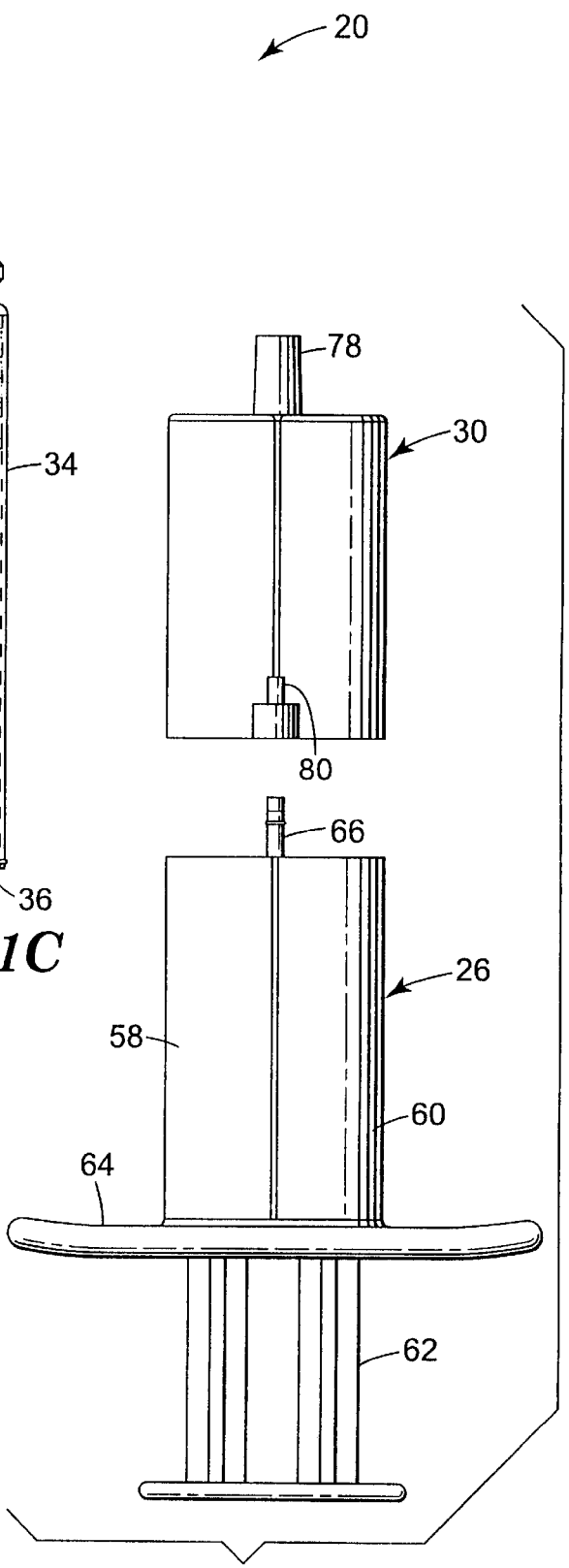
Fig. 1B
Fig. 1C
Fig. 1D
Fig. 1A

DISPENSER FOR AN ADHESIVE TISSUE SEALANT HAVING A HOUSING WITH MULTIPLE CAVITIES

CROSS REFERENCE TO RELATED APPLICATION

This application is a continuation-in-part of U.S. patent application Ser. No. 08/956,308, filed Oct. 22, 1997.

TECHNICAL FIELD

The invention relates generally to the dispensing of adhesive tissue sealants and other liquid preparations, including those requiring mixing immediately prior to use.

BACKGROUND

A variety of techniques have been used to bond or seal living tissue. For example, different types of tissues have been mechanically bound or sealed with a number of procedures, materials and methods including sutures, staples, tapes and bandages. In some applications, these materials are made of absorbable materials that are intended to bond and/or seal tissue as it heals and then to be absorbed over a period of time.

A recent addition to the techniques that can be used is application of an absorbable adhesive sealant composition to bond and/or seal tissue. The adhesive composition is readily formed from a two component mixture that includes a first part of a cross-linking agent and a second part of a protein, preferably a serum protein such as albumin. When the two parts of the mixture are combined, the mixture is initially liquid. The combined mixture then cures in vivo on the surface of tissue to give a substantive composition that securely bonds to the tissue. Additional details can be found in commonly owned U.S. Pat. No. 5,583,114, "ADHESIVE SEALANT COMPOSITION," to Barrows et al, the entire contents of which are hereby incorporated by reference.

Among the limitations on the widespread use of this material are that the first part, when rehydrated, has a limited shelf life and must be dissolved relatively shortly before use. Another limitation is that the two parts must be kept strictly separate until dispensed onto the tissue because the reaction time of the forming of the finished sealant is quite fast. These limitations increase the complexity for appropriate dispensing by the medical practitioner to form an effective adhesive tissue sealant on the tissue surface.

A known approach for dispensing two-part tissue sealants is to supply the user with a kit consisting of at least two syringes, vials containing the components in dry powder form, a syringe body for receiving and supporting both syringes, and a housing for connecting the two syringes to a common nozzle. The user fills the syringes by piercing the septums on the vials and withdrawing solution into the barrel of the syringe. If a component is in powder form within a vial, the user first injects a solvent and then withdraws the reconstituted solution. The needles on the syringes are removed, the syringe barrels and plungers are supported in housing, and the syringe nozzles are received in the housing.

Another approach is disclosed in U.S. Pat. No. 4,735,616 to Eibl. Dry powder is stored within both barrels of a dual barrel syringe. In each instance, the powder is stored on one side of a sliding plug, and solvent is stored on the other side. When the user presses down on the syringe plunger, the plugs slide along the barrels to positions at which the barrels each have a bulge that provides a bypass for the solvent to reach the powder.

In these prior art dispensers, the manifold passages connecting the two syringes to the common nozzle are typically narrow conduits of circular cross section. E.g., U.S. Pat. No. 4,631,055 to Redl.

Carpules have been used in some syringes; e.g., U.S. Pat. No. 3,767,085 to Cannon shows a dual carpule syringe for mixing compositions used in dentistry.

A kit for reconstitution and application of Tisseel® fibrin sealant including VH Sealer Protein and Thrombin solutions is currently available from Baxter Healthcare Corporation's division of Glendale, Calif. The use of this product requires a complicated procedure. As a result, it is difficult to prepare the fibrin sealant with this kit and it is also difficult to use the applicator. Additionally, the applicator is said to suffer from clogging problems.

The Tisseel® kit comprises a first bottle containing freeze-dried thrombin, a second bottle with calcium chloride solution designed to reconstitute the thrombin; a third bottle with sealer protein concentrate, and a fourth bottle with fibrinolysis inhibitor solution. A Fibrinotherm® Heating and Stirring Device is used to heat and stir the components such as the sealer protein concentrate and the fibrinolysis inhibitor solution. Alternatively, a hot water bath or incubator may be used. This requires components to be heated above room temperature prior to use, further complicating the procedure.

The packaging of this device also causes problems. Two syringes and at least two (and preferably four) exposed needles are required simply to reconstitute the thrombin and sealer protein concentrate. For transfer of the Tisseel® VH solution and the Thrombin Solution to the sterile field in the operating room, the scrub nurse should withdraw the solutions while the circulating nurse holds the unsterile vials. This requires the coordination of two healthcare workers, one of which directs a sharp instrument (needle) toward the other. This is required twice to prepare the applicator of the product.

The packaging also includes multiple pouches that contribute to the waste and clutter at the location of medical care.

Outside the United States, a kit is available for use in preparing and dispensing the Beriplast® fibrin adhesive. This kit includes four vials with fibrinogen concentrate in a first vial, aprotinin solution in a second vial, thrombin in a third vial and calcium chloride solution in a fourth vial. An adapter with dual piercers is available in some kits which helps place the contents of one vial into another. However, once the two components of the fibrin adhesive are in solution form, the kit nevertheless requires two exposed needles to transfer the solutions from the mixed vials into the separate syringes of the delivery device. Since the external portion of the vials are considered non-sterile (i.e. all four vials are packaged in a box), it is believed that this kit also requires the coordination of two healthcare workers (one associated with the sterile field, one outside), one of which directs a sharp instrument (needle) toward the other.

SUMMARY OF THE INVENTION

The present invention provides an improved dispenser suitable for quickly and easily setting up and dispensing multi-part tissue sealants or other multi-part compositions requiring separation of the components until just prior to application on the tissue surface.

In a first aspect, the invention features a dispenser having a container (e.g., a carpule) with at least a portion of a first component of a multi-part tissue sealant and/or adhesive (e.g. a dry powder) having a septum at one end, an open end opposite the septum, and a movable plug. The powder may be retained at the septum end of the container by the movable plug, which is preferably displaced and pushed back as a solvent used for reconstituting the powder is introduced (e.g., through the septum). At least a portion (and preferably all) of a second component of the tissue sealant (e.g. a liquid) is contained within a second container, also with a movable plug. After the first component is reconstituted, a housing (preferably a manifold) having piercers is used to pierce both septums and allow the contents to be dispensed. Preferably, the piercers are placed in a protected position so as not to expose a user to contact with the piercers. A body supports the containers. Pistons are provided to advance the movable plugs.

Preferred implementations of the first aspect may include one or more of the following features.

The first component may be a dry powder of a water-compatible or water-soluble cross-linking agent.

The aqueous solution for dissolving the powder may be introduced through the first septum (e.g., either via the piercer or via an injection through the septum by a syringe).

The movable plug may be positioned in a position in which the space between the plug and the septum is substantially the minimum necessary to contain the dry powder, thereby reducing the amount of air in that space and consequently the amount of pressure rise associated with injecting liquid through the septum. The movable plug can move away from the septum as liquid is injected to reduce any pressure rise.

The second component stored in the second carpule may be a solution.

The second component may be a protein dissolved in an aqueous buffer and capable of reacting with the solution of the first component to provide the adhesive tissue sealant.

The body may comprise a retainer for protecting and/or holding the containers.

In a second aspect, the invention features an improved manifold for a two-part dispenser. Two containers (e.g., carpules), each having a septum at one end, an open end opposite the septum, and a movable plug, are supported in a dual syringe body, which has pistons configured to enter the open ends of the containers to advance the movable plugs. A manifold has cavities that receive the septum ends of the containers, and a disk supporting a piercer (e.g., hollow needle) is mounted in the base of each cavity so that the septum of a container is pierced when it is installed in a cavity. Each disk is supported a distance above the base of a cavity to form a plenum defined by the disk and adjacent walls of the base of the cavity. Liquid exiting a container travels through the lumen of the piercer, then into the adjacent plenum, and then out of the plenum along a conduit extending to the nozzle. This arrangement of disks each supporting a piercer and forming a plenum provides an effective, relatively low-cost way of constructing a manifold for connecting carpule piercers to a common nozzle.

Preferred implementations of the second aspect may include one or more of the following features.

Each disk may be sealed to the surrounding wall of the cavity (e.g., by an elastomeric sealing member on the disk) so that the adjacent plenum is defined by the disk and the base of the cavity.

The conduit and piercer lumen may each communicate with the plenum at laterally spaced apart locations so that flow from the piercer lumen to the conduit changes direction from a generally longitudinal flow path through the piercer lumen, to a generally lateral direction in the plenum, and then to a generally longitudinal flow path in the conduit.

The disk may be supported from the base of the cavity by standoffs.

The first container may contain a quantity of the first component in the form of a dry powder so that the first component must be dissolved prior to use by introduction of an aqueous solvent.

The second container may contain a quantity of protein in an aqueous buffer that is capable of reacting with a dissolved first component to provide an adhesive tissue sealant.

In a third aspect, the invention features a method for dispensing a component stored in a dispenser in dry powder form and reconstituted by introduction of a solvent. A carpule is provided with a septum at one end, an open end opposite the septum end, and a movable plug disposed therebetween. The dry powder is stored between the septum and the movable plug. Solvent is introduced into the interior of the container by piercing the septum with a syringe and injecting the solvent into the carpule. The carpule is installed in a syringe body and manifold, the latter providing a flow path from the piercer to an outlet nozzle.

Preferred implementations of the third aspect may include one or more of the following features.

Installing the carpule in the syringe body and manifold may occur before or after the solvent is injected through the septum.

The first movable plug may be positioned in a position in which the space between the plug and the septum is substantially the minimum necessary to contain the dry powder, thereby reducing the amount of air in that space and reducing the pressure increase within the carpule when the solvent is introduced by piercing the first septum. The movable plug can move away from the septum as liquid is injected to reduce any pressure rise.

The dispenser may comprise a second carpule comprising a second septum at one end, an open end opposite the second septum, and a second movable plug disposed therein, the second carpule containing a second component, and the syringe body and manifold may be sized and configured to accept the first and second carpule.

The second component may be a protein in an aqueous buffer and capable of reacting with the first component to provide an adhesive tissue sealant.

The dry powder of the first component may be a water-compatible or water-soluble cross-linking agent capable of reacting with the second component to provide the adhesive tissue sealant.

In another aspect, the present invention comprises a kit having components useful for preparing and delivering a tissue sealant and/or adhesive having first and second components. The kit comprises a first container having a septum, at least a portion of the first component stored therein, and outer portions. The kit includes a second container having at least a portion of the second component therein, a septum, and outer portions. At least one vial with a solvent for at least one of the first and second components is also present in the kit. The kit further includes a syringe and needle; and a sterile housing having first and second piercers located in protected positions and a portion that is sized and shaped to receive the first and second containers.

In another aspect, the present invention comprises a method of preparing a multiple component tissue sealant and/or adhesive just prior to use comprising the steps of providing a first container having a septum and a dry powder stored therein; providing a second container having a septum and a liquid therein; providing a vial with a solvent for the dry powder therein; providing a syringe and needle; providing a housing having first and second piercers located in protected positions and a portion that is sized and shaped to receive the first and second containers; withdrawing the solvent from the vial with the syringe and needle; placing the solvent in the first container; and installing the first and second containers in the housing and piercing the septums of the first and second containers with the first and second piercers without exposing a user to physical contant with the piercers.

The invention provides a significantly simpler and easier to use dispenser, one particularly well suited to handling adhesive tissue sealants. It is also simple and relatively inexpensive to manufacture. It delivers excellent performance, and is particularly good at mixing solutions reconstituted from dry powder.

Other features and advantages of the invention will be apparent from the following description and drawings, and from the claims.

BRIEF DESCRIPTION OF THE DRAWINGS

FIGS. 1A–1D are side views of elements of a preferred embodiment of the invention;

FIGS. 18 through 26 illustrate steps in the use of a kit according to one aspect of the present invention wherein FIG. 18 illustrates a syringe and needle being loaded with a solvent;

FIG. 19 illustrates the loaded syringe (after being loaded with solvent in the operation depicted in FIG. 18) being used to fill a first container with the solvent to dissolve a first component of a tissue adhesive and/or sealant within the first container;

FIG. 20 illustrates optional additional manual mixing of the first component of a tissue adhesive and/or sealant within the first container;

FIG. 21 illustrates a container being loaded into the housing of a tissue adhesive and/or sealant dispenser;

FIG. 22 shows a dual piston being received in open ends of first and second containers of the dispenser;

FIG. 23 illustrates an optional step of expressing air from the dispenser preassembly;

FIG. 24 illustrates an optional step of cleaning the surface of the housing of the dispenser;

FIG. 25 shows a dispensing tip being attached to the dispenser; and

FIG. 26 illustrates the assembled dispenser being used to dispense a tissue adhesive and/or sealant composition.

DETAILED DESCRIPTION

Figure 2:
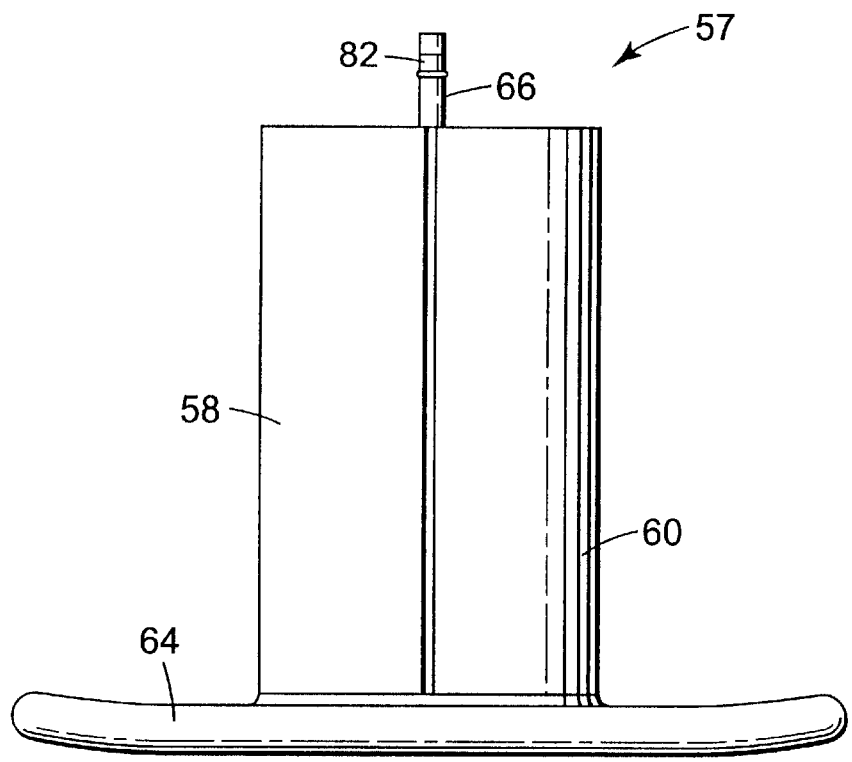
FIG. 2 is a side view of the base of the dual syringe body.

Referring now to FIGS. 1A–1D, side views of an example of the elements of a dispenser kit 20 according to the present invention are illustrated. The dispenser kit 20 includes a first carpule 22, a second carpule 24, a dual syringe body 26 adapted to receive and support the first and second carpules, a syringe 28, and a manifold (nozzle body) 30. First carpule 22 has a first septum 32 at one end of first carpule body 34, the other end of the first carpule body being an open end 36. There is a first movable plug 38 disposed within the first carpule 22 so that a quantity of a first component 40 is contained between the first septum 32 and the first movable plug. In preferred embodiments, first component 40 is a quantity of dry powder of a water-compatible or water-soluble multi-functional cross-linking agent. Conveniently, the first carpule body 34 has a ridge 42 near open end 36 to facilitate the retaining of the first carpule within dual syringe body 26.

First movable plug 38 is positioned so that the space between the plug and the septum is substantially the minimum necessary to contain the dry powder, thereby reducing the amount of air in the space between the plug and septum. Reducing the amount of air entrapped with the powder has the benefit that when solvent is injected into the carpule to dissolve the powder there is less rise in pressure within the carpule, as the plug is able to move away from the septum to reduce any pressure rise. Elevated pressure is undesirable in that it could lead to difficulty when the solvent is injected into the carpule and when the carpule is later pierced on insertion in the manifold 30. An elevated pressure could result, once piercing occurs, in immediate flow of the first component into the manifold and nozzle.

Second carpule 24 has a second septum 44 at one end of second carpule body 46, the other end of the second carpule body being an open end 48. There is a second movable plug 50 disposed within the second carpule 24 so that a quantity of a second component 52 is contained between the second septum 44 and the second movable plug. In preferred embodiments, second component 52 is a quantity of protein in an aqueous buffer. Conveniently, the second carpule body 46 has a ridge 56 near open end 48 to facilitate the retaining of the second carpule within dual syringe 26.

Preferably, first and second movable plugs 38 and 50 include a lubricant. In a preferred embodiment, the lubricant comprises a coating of silicone. The lubricant facilitates movement of the plugs relative to the rest of the containers 22 and 24.

Also preferably, the first and second septums 32 and 44 are fixed to the containers (e.g. carpules) 22 and 24 by aluminum caps. The elongate cylindrical portion of the containers 22 and 24 may be glass in one preferred embodiment. The glass allows the user to see the contents of the containers 22 and 24.

Dual syringe body 26 includes a base 57 having two cylinders 58 and 60 adapted to receive and support the first and second carpules 22 and 24. A dual piston 62 is provided, adapted to enter the open ends 36 and 48 of the carpules 22 and 24 so as to contact and advance the first and second movable plugs 38 and 50. A flange 64 is provided to allow the practitioner to grip the dual syringe body 26 during injection in the conventional manner for syringes. A pair of latches 66 (only one being visible in this view) are provided to attach dual syringe body 26 to manifold 30.

Syringe 28 is conveniently of conventional type, having a body 68, a nozzle or needle 70 at one end, and a piston 72 at the other end. A protective cap 74 is provided to preserve the needle 70 in a sterile condition until the kit is to be used. The needle 70 is adapted to pierce the first septum 32 for injecting the aqueous solvent 76 contained within syringe 28 into the first carpule 22. In a preferred embodiment, solvent 76 is pyrogen free sterile water (e.g. USP water for injection) for dissolving the dry powder of a water-compatible or watersoluble multi-functional cross-linking agent.

Manifold 30 is adapted to fit over and pierce the first and second septums 32 and 44 after the first component 40 has been mixed with the solvent 76. Manifold 30 has a dual nozzle 78, which in the preferred embodiment keeps the first and second components 40 and 52 completely separate until just after the moment of dispensing. A pair of receptacles 80 (only one being visible in this view) are provided to attach dual syringe body 26 to manifold 30 by receiving latches 66. Optionally, the kit 20 may include a static mixer and/or dispensing tip that is adapted to be fitted onto nozzle 78.

Figure 3:
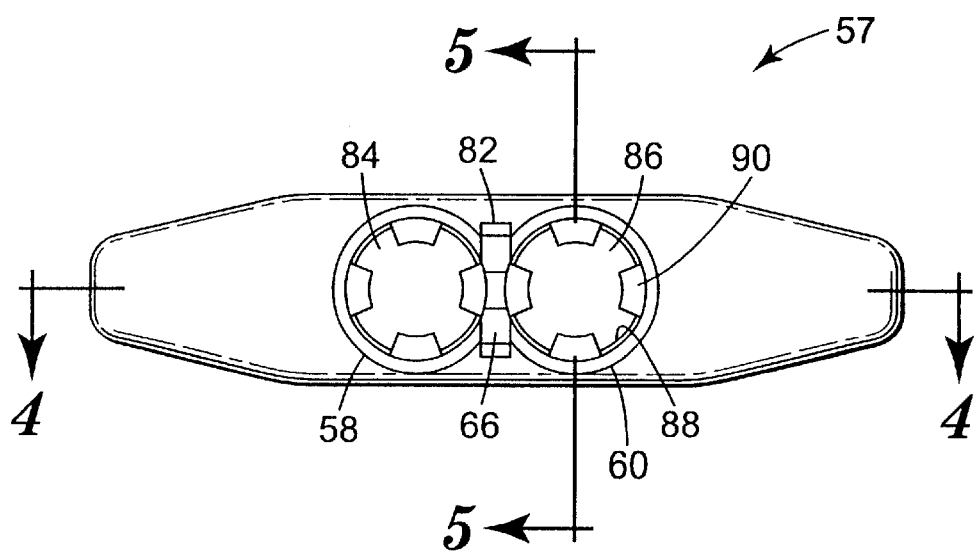
FIG. 3 is a bottom view of the base of FIG. 2.

Referring now to FIG. 2, a side view of the base 57 of the dual syringe body 26 is illustrated in isolation. It will be noted that the latches 66 each have a projection 82 which allows them to interact with the receptacles 80 as discussed above. Referring now to FIG. 3, a bottom view of the base 57 of FIG. 2 is illustrated. In this view it can be seen that cylinders 58 and 60 have internal through bores 84 and 86 respectively which are sized to receive first and second carpules 22 and 24 (shown in FIGS. 1A–1D). It can also be seen that projecting inwards from the walls of each of the cylinders 58 and 60 are four tapered ledges 88 which interact with ridges 42 and 56 of first and second carpules 22 and 24 respectively to retain the carpules within the bores 84 and 86.

Figure 4:
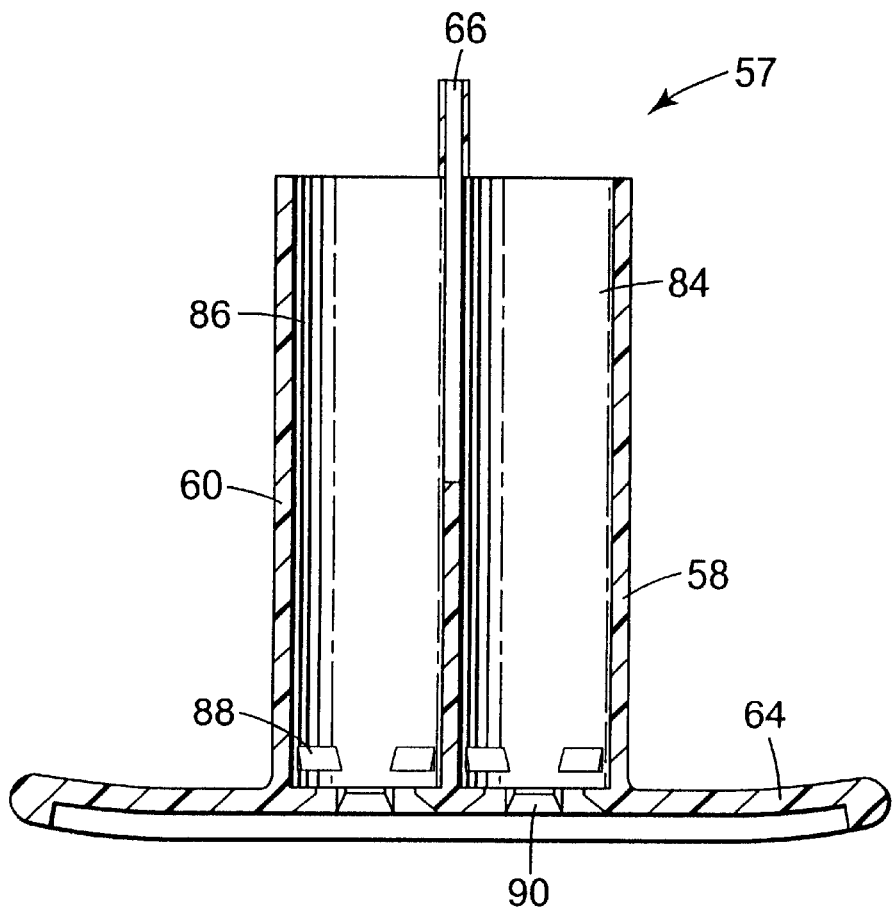
FIG. 4 is a cross-sectional view taken along section lines 4—4 in FIG. 3.
Figure 5:
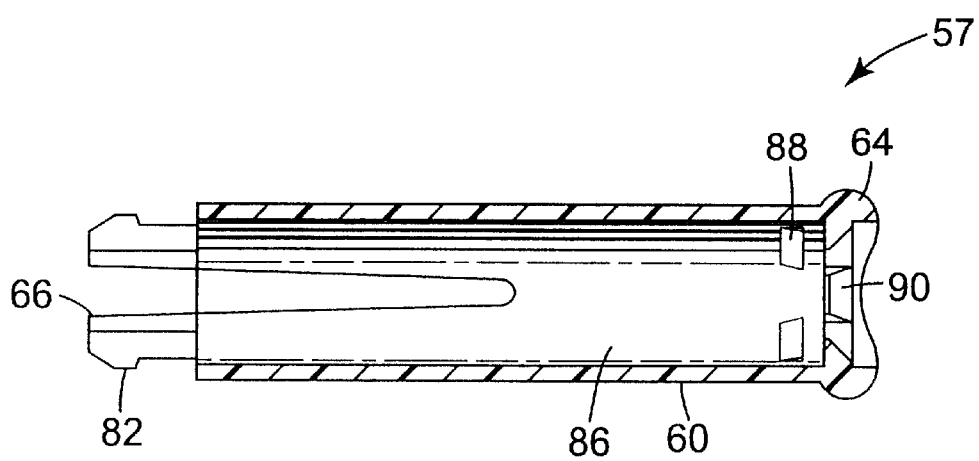
FIG. 5 is a cross-sectional view taken along section lines 5—5 in FIG. 3.

Referring now to FIG. 4, a cross-sectional view of base 57 taken along section lines 4—4 in FIG. 3 is illustrated. In this view it can be seen that projecting inwards from the walls of each of the cylinders 58 and 60 are four tapered retainers 90 which interact with and retain dual piston 62 within the bores 84 and 86. This will be discussed in more particularity below. In FIG. 5, a cross-section view of base 57 taken along section lines 5—5 in FIG. 3 is illustrated so that the features of the base can be more readily seen.

Figure 6:
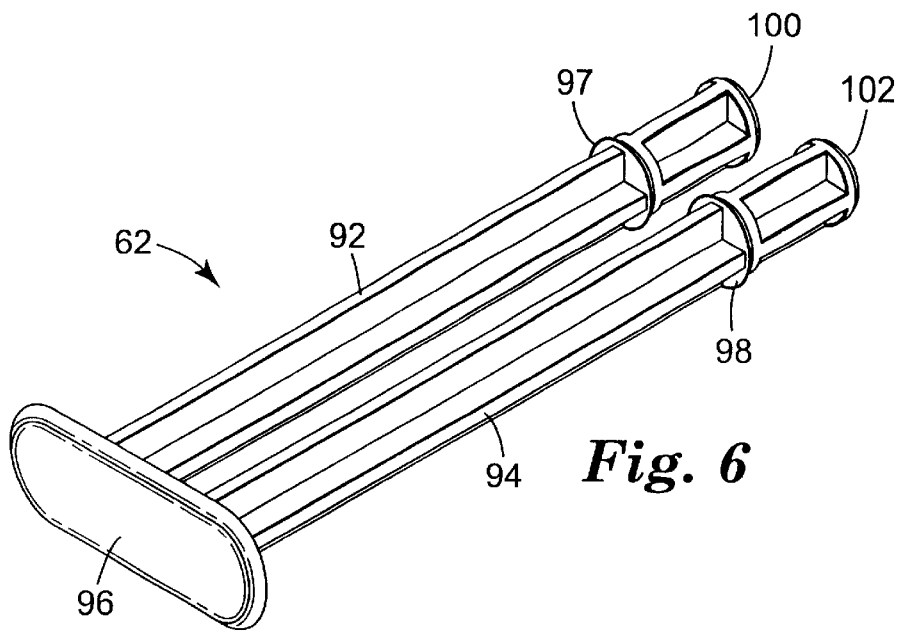
FIG. 6 is a perspective view of the dual piston.
Figure 7:
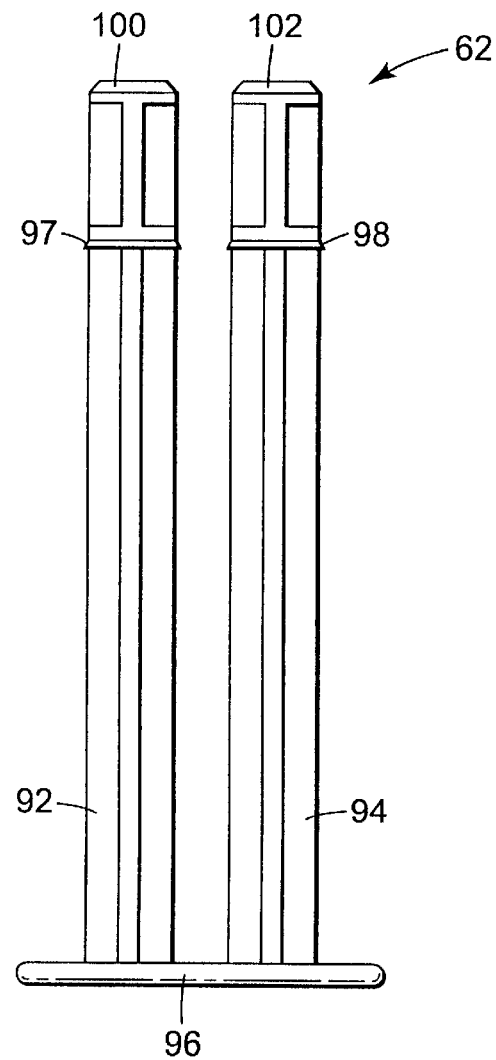
FIG. 7 is a side view of the dual piston of FIG. 6.

Referring now to FIGS. 6 and 7, views of dual piston 62 are illustrated. A pair of push rods 92 and 94 extend from a thumb plate 96. Each of the push rods 92 and 94 has a circumferential ridge 97 and 98 adapted to interact with the tapered retainers 90 discussed in connection with FIGS. 4 and 5 to retain dual piston 62 within bores 84 and 86. The free ends 100 and 102 are intended to contact movable plugs 38 and 50 (seen in FIGS. 1A–1D) to advance them and pressurize the fluid in carpules 22 and 24 when pressure is exerted by the hand of the practitioner on the thumb plate 96.

Figure 8:
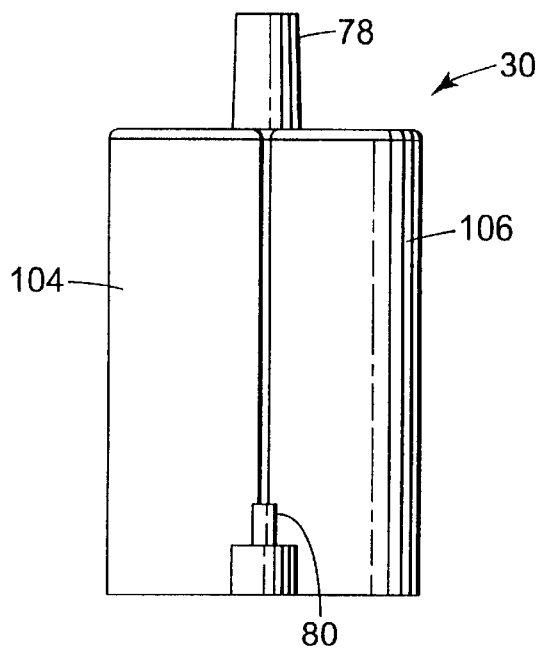
FIG. 8 is a side view of the manifold.

Referring now to FIG. 8, a side view of the manifold 30 is illustrated in isolation. The manifold 30 includes barrels 104 and 106 which are sized and shaped to enclose the ends of the of carpules 22 and 24 having septums 32 and 44 when the carpules have been inserted into the base 57 and the manifold has been attached to the base by interlocking latches 66 with receptacles 80.

Figure 9:
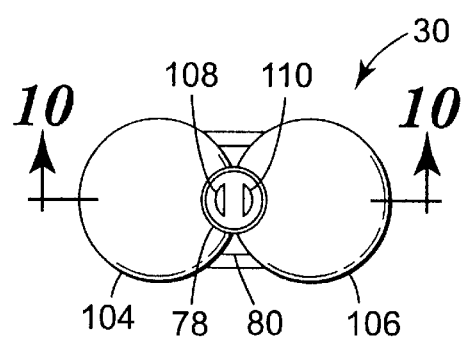
FIG. 9 is a bottom view of the manifold of FIG. 9.

Referring now to FIG. 9, a bottom view of manifold 30 of FIG. 8 is illustrated. In this view it can be seen that nozzle 78 includes openings 108 and 110 to allow the components in carpules 22 and 24 to be dispensed as separate solutions. A further nozzle element (not shown) could be installed over nozzle 78 to contain and promote mixing of the two streams of liquid emerging from openings 108 and 110.

Figure 10:
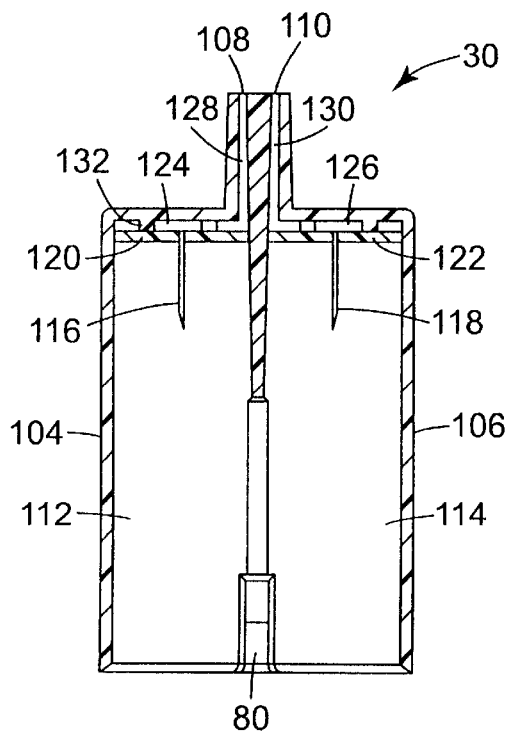
FIG. 10 is a cross-sectional view taken along section lines 10—10 in FIG. 9.

Referring now to FIG. 10, a cross-sectional view taken along section lines 10—10 in FIG. 9 is illustrated. It can now be seen that barrels 104 and 106 have cylindrical, hollow interiors (or cavities) 112 and 114 respectively to receive the carpules 22 and 24. A pair of piercers 116 and 118 are provided to pierce the septums 32 and 44 when the manifold 30 is mounted on the base 57. The piercers are conveniently mounted on mounting disks 120 and 122, the edges of which form a seal with the walls of cylinders 104 and 106. This may be conveniently accomplished by solvent bonding, by ultrasonic welding, or by having an elastomeric member (e.g., an o-ring within a groove) along the edge of the mounting disks 120 and 122 which contact the walls 104 and 106 and hold the mounting disks 120 and 122 in place by friction fit. Access is available for the contents of carpules 22 and 24 through the hollow central bore of each of the piercers into plenums 124 and 126 and on into passageways (or conduits) 128 and 130 to openings 108 and 110. Several standoffs 132 are conveniently molded into the base of cavities 112 and 114 to position the mounting disks 120 and 122 in the right location to provide for plenums 124 and 126.

The dispenser kit is easily sterilized. In one embodiment, the carpules can be sterile filled or e-beam sterilized, and the assembled kit undergoes a terminal sterilization (e.g., with ethylene oxide gas or gamma or e-beam irradiation).

Figure 11:
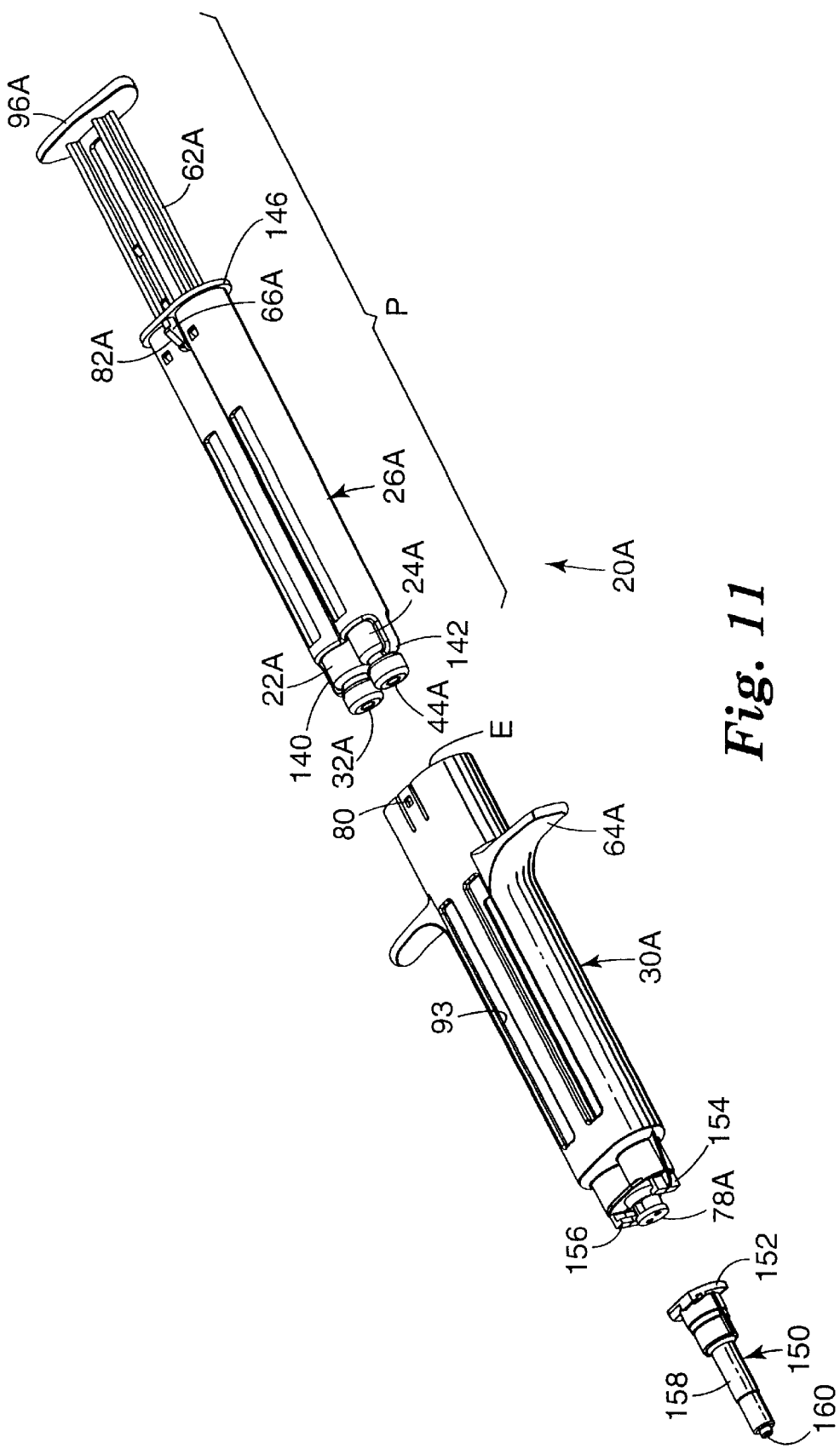
FIG. 11 is a perspective exploded view of elements of an alternate embodiment of the invention.

Referring now to FIG. 11, a perspective view of an alternate embodiment of several of the elements of a dispenser 20A according to the present invention is illustrated. The dispenser 20A includes first container 22A and second container 24A with movable plugs 38A and 50A; housing 30A and a dual syringe body 26A. The dual syringe body 26A is sized and shaped to receive and support the containers 22A and 24A.

The housing 30A includes a manifold. Latches 66A (only one being visible in FIG. 11) are provided to attach dual syringe body 26A to housing 30A. The latches 66A are preferably located at the proximal end of the dual syringe body 26A. The latches 66A preferably include projections 82A that are still sized and shaped to be received in receptacles 80A in the housing 30A so as to snap-connect the housing 30A to the dual syringe body 26A.

Optionally, the containers 22A and 24A (preferably carpules), dual syringe body 26A and piston 62A may be brought together into a preassembly P as shown in FIG. 11. The preassembly P makes the task of insertion of the containers 22A and 24A into the housing 30A more convenient as a user can accomplish this by simply sliding the preassembly into the housing.

Alternatively, the latches 66A, projections and receptacles 80A may be sized and shaped so that preassembly P may be easily, manually removed from the housing 30A. The latches 66A, projections and receptacles 80A are designed so that the preassembly P may be manually releasable. In some surgical procedures, it may be desirable to replace spent carpules with new carpules. With the embodiment described with releasable latches, it can be seen that at least portions of the dispenser 20A may be reused. This can be especially suitable in surgical procedures that require multiple sets of carpules to deliver the tissue adhesive or sealant. Preferably, the dispenser according to the present invention is only reusable on the same patient. After the surgical procedure on the patient, the dispenser is discarded.

Finger flange 64A is provided on the housing 30A to allow the practitioner to grip the dispenser in the conventional manner. Finger springs 140 and 142 engage the shoulders of the carpules 22A and 24A to retain first and second carpules 22A and 24A within the dual syringe body 26A. A limiting shoulder 146 interengages with the proximal end E to limit the extent to which the syringe body 26A may be inserted into the housing 30A. The element that includes limiting shoulder 146 may have a hole that is sized and shaped to engage legs 92A and 94A of dual piston 62A to retain the association of the dual piston 62A with the inner portions of the carpules 22A and 24A. As a result, the tapered retainers 90 of the embodiment shown in FIG. 3 are not needed in this embodiment.

The preassembly P is readily manufacturable as the construction of the finger springs 142 and 144 is less sensitive to tolerances than the design shown in FIGS. 1–10.

The dispenser 20A may optionally include a separate dispensing tip 150 that is sized and shaped to be fitted onto nozzle 78A. The dispensing tip 150 preferably includes a base flange 152 that is adapted to engage complementary grips 154 and 156 adjacent the nozzle 78A. In a preferred embodiment, the dispensing tip 150 has a static mixing element within its barrel 158, although this is not shown in FIG. 12. Preferably, the dispensing tip 150 includes a fluidic element 160 at the tip to provide a final mixing of the two liquid components just before dispensing. Preferably, the orifice of the dispensing tip is approximately circular and between about 0.005 inches to 0.010 inches (0.012 to 0.025 mm) in diameter and about 0.003 inches (about 0.0762 mm) in length. A length to diameter of the orifice of no more than 1:2 is preferred.

Figure 12:
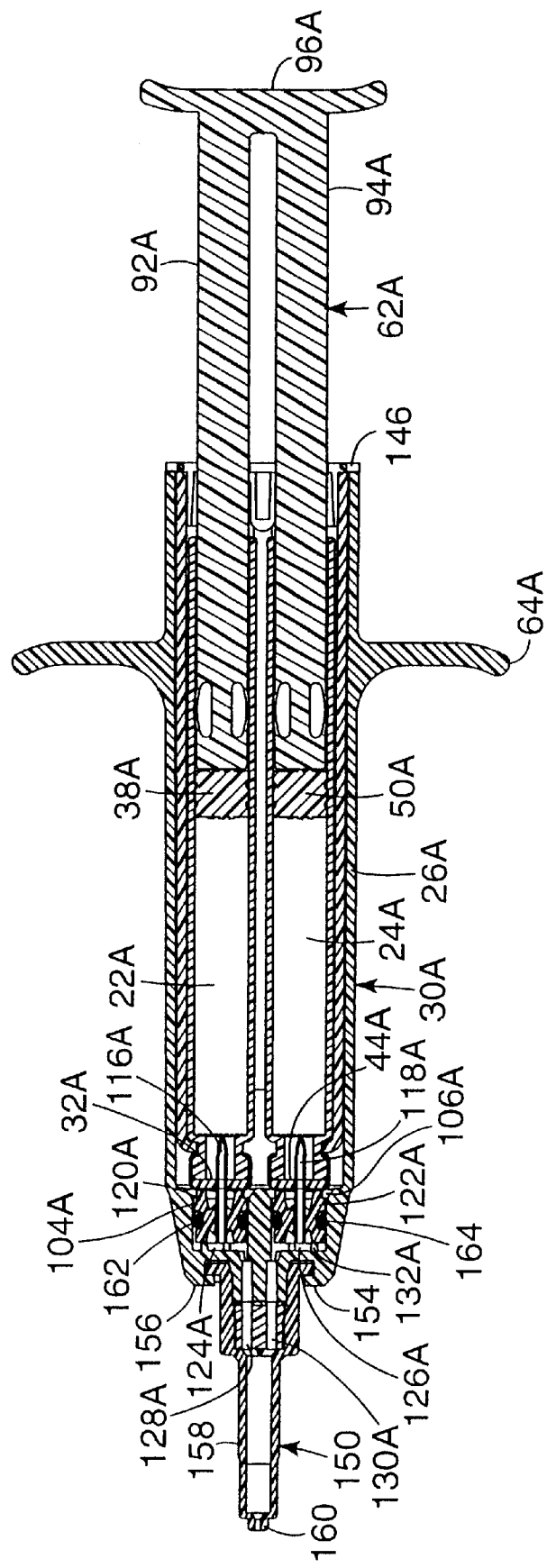
FIG. 12 is a cross-section front view of the assembled alternate embodiment of FIG. 11.

Referring now to FIG. 12, a cross-section front view of the assembled embodiment of FIG. 11 is illustrated. The details of the manifold are best seen in this view. The manifold includes piercers 116A and 118A that are situated in protected positions. By "protected positions" it is meant that a user could not readily engage the sharp surfaces of the piercers 116A and 118A. In preferred embodiments, such contact is very difficult and the likelihood of it happening is substantially reduced. Preferably, the first and second septums 32A and 44A do not contact the piercers 116A and 118A until the containers 22A and 24A are substantially inside housing 30A.

Referring to FIG. 11, if the housing 30A is opaque, the housing 30A may optionally include viewing windows or slots. The viewing windows 93 may be especially desirable if the housing 30A is constructed from a material that is opaque or if the housing is otherwise difficult to see through. The windows 93 allow the user to view the remaining portions of the tissue adhesive and/or sealant in the containers 22A and 24A. The windows 93 are preferably thin and elongate so as to substantially reduce that chance that the user will come into contact with the piercers 116A and 118A.

The piercers 116A and 118A are mounted on mounting disks 120A and 122A, the edges of each of which form a seal with the walls of cylinders 104A and 106A by means of O-rings 162 and 164. Mounting disks 120A and 122A are situated against standoffs 132A to create plenums 124A and 126A. The first and second components of the tissue sealant or adhesive may flow through passageways or conduits 128A and 130A. Once the components of the tissue sealant or adhesive exit the passageways 128A and 130A, they can then begin mixing in the dispensing tip 150. The dispensing tip 150 may be made in accordance with the teachings of Atomization and Sprays, by Arthur H. Lefebvre (published by Hemisphere Publishing Corporation, U.S.A. 1989) (the entire contents of which are herein incorporated by reference with specific reference to pages 112–121). Preferably, a static mixer within dispensing tip 150 is constructed to afford mixing of the first and second components of the tissue sealant or adhesive. For example, the static mixer may comprise a static mixer similar to the static mixers taught in U.S. Pat. Nos. 5,080,493 and 5,386,928 (the entire contents of which are herein incorporated by reference).

Flange 64A is provided to allow the practitioner to grip the housing 30A during injection in the conventional manner for syringes. The finger flange 64A is sized and shaped to afford convenient manual grasping.

Figure 13:
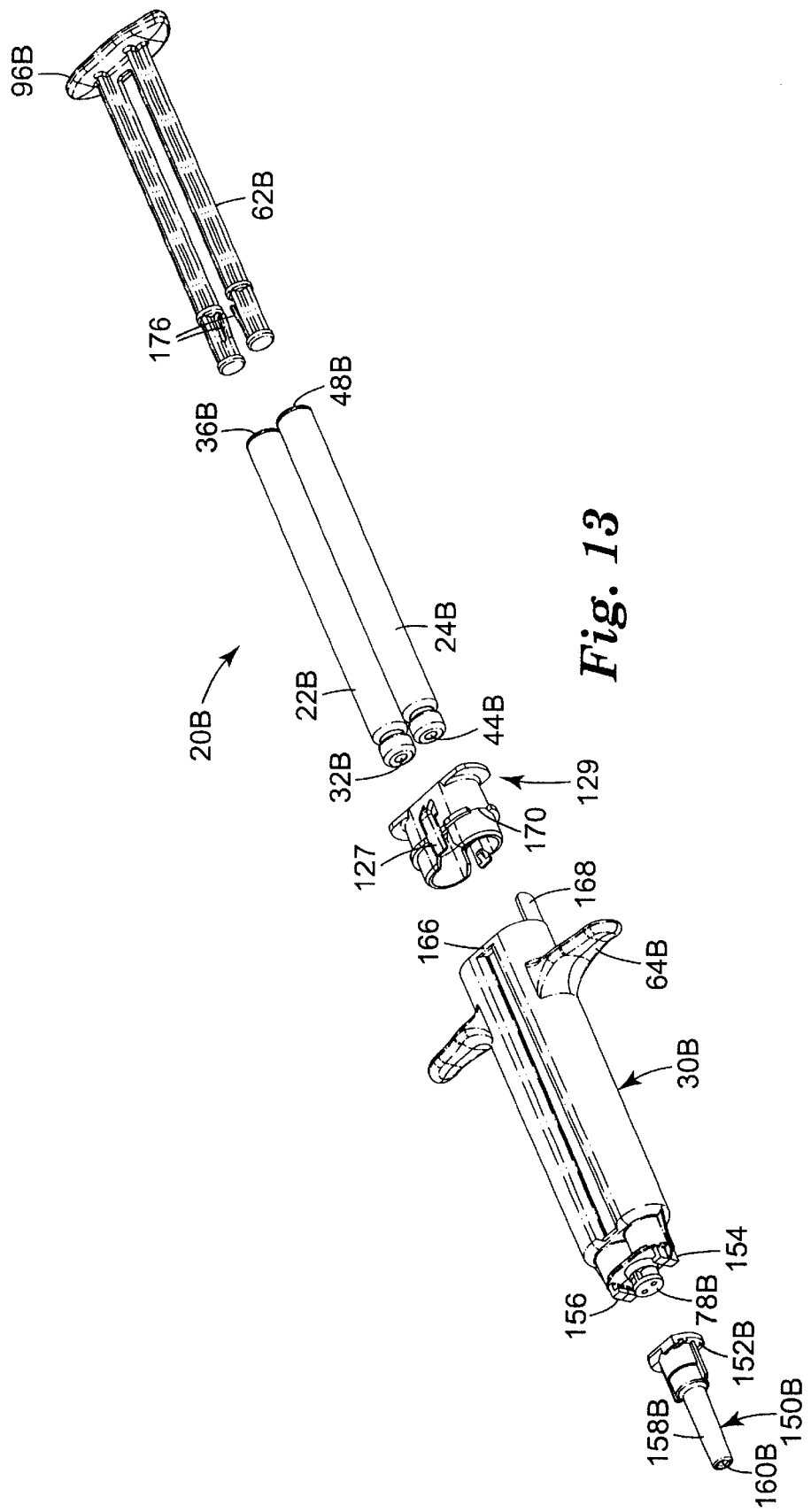
FIG. 13 is a perspective exploded view of elements of an additional alternate embodiment of the invention.
Figure 14:
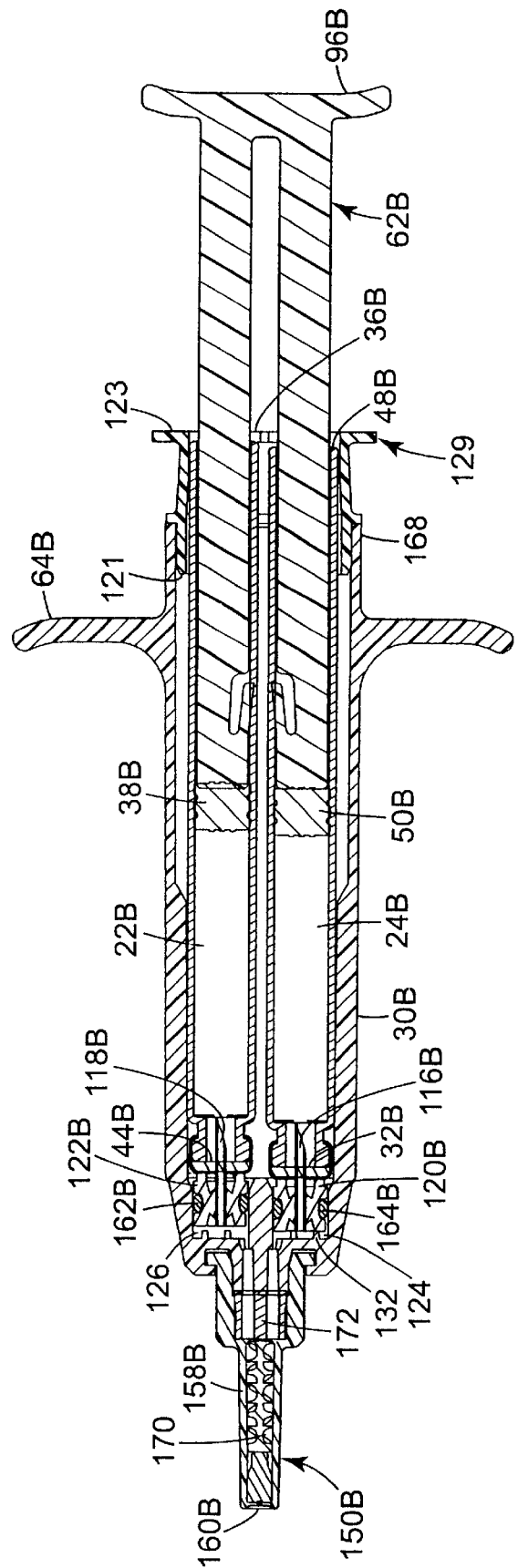
FIG. 14 is a cross-section front view of the assembled alternate embodiment of FIG. 13.

Referring now to FIGS. 13 and 14, a perspective exploded view and an assembled view of an additional alternate embodiment are illustrated. The dispenser 20B includes a housing 30B with a manifold, containers 22B and 24B, and dispensing tip 150B. The dispenser 20B is particularly suitable for simultaneously dispensing first and second components of a tissue sealant, such as, for example, the tissue sealant and/or adhesive disclosed in U.S. Pat. No. 5,583,114 to Barrows et al. Preferably, at least the first component is initially stored and/or shipped in the dispenser as dry powder. For example, the first component may initially comprise 130 mg Poly (ethylene glycol) di-succinimidyl succinate (PEGSS2) in powder form that is designed to be dissolved just prior to use by introduction of a solvent (e.g. about 1 ml of sterile water). Alternatively, for medical procedures that require additional amounts of tissue sealant, the first component may comprise 260 mg of PEGSS2 in powder form that is designed to be dissolved just prior to use by about 2 ml of sterile water.

The dispenser 20B comprises a first container 22B having a first septum 32B at one end, an open end 36B opposite the first septum, and a first movable plug 38B disposed therein. The first container 22B initially contains a quantity of the first component in the form of a dry powder stored between the first septum 32B and the first movable plug 38B. The first component is preferably stored and/or shipped in a dry powder/separate solvent solution until just prior to use of the dispenser 20B to deliver or apply a tissue sealant and/or adhesive to a patient. Just prior to use of the dispenser 20B to deliver or apply a tissue sealant and/or adhesive to a patient, the dry powder may be dissolved in a solvent. FIG. 14 illustrates the container 22B after the solvent has been added and air has been expunged.

The dispenser 20B includes a second container 24B comprising a second septum 44B at one end, an open end 48B opposite the second septum 44B, and a second movable plug 50B disposed therein. The second container 24B contains a quantity of the second component, preferably in liquid form (e.g. 1 mL Human Serum Albumin solution). Preferably, the second component is stored and shipped in this liquid form.

The dispenser 20B includes housing 30B having internal surfaces with first and second piercers 116B and 118B that are preferably sharp to pierce the first and second septums of the first and second containers 22B and 24B. The first and second piercers 116B and 118B are situated in protected positions so that the first and second septums may be pierced without exposing a user to contact with the first or second piercers 116B and 118B. The housing 30B affords passage of the first and second components via first and second flow paths to a nozzle 78B from which the first and second components are dispensed to combine to form the adhesive tissue sealant.

Pistons are sized and configured to be received in the open ends 36B and 48B of the first and second containers 22B and 24B to advance the first and second movable plugs 38B and 50B. Preferably, the pistons are provided by dual piston 62B.

A manually removable dual body in the form of retainer 129 is sized and shaped to receive the containers 22B and 24B. The retainer 129 protects and supports the containers 22B and 24B. The retainer 129 is particularly suitable when the containers 22B and 24B are constructed from glass that may be broken.

The retainer 129 may engage the proximal end of the housing 30B. Preferably the retainer 129 includes attachment means for releasably engaging the housing 30B. In a preferred embodiment, the attachment means are manually releasable and may reattach the retainer 129 to the housing 30B. The retainer 129 may, for example, be held onto the housing 30B by a press fit, or conveniently have an extending arm 127 which latches over a lip 166 near the proximal end of the housing 30B.

As best seen in FIG. 14, the retainer 129 preferably includes a distal end 121 and a proximal end 123 having an opening. The containers 22B and 24B are received in the opening of the retainer 129. The containers 22B and 24B can be easily slid through the retainer 129 so that the septums 32B and 44B may be pierced by piercers 116B and 118B. Also preferably, the retainer 129 is sized and shaped so that the open ends 36B and 48B of the first and second containers 22B and 24B do not project substantially beyond the opening of the retainer.

It may sometimes be desirable to reuse the same housing 30B during a surgical procedure on a single patient. This may be accomplished by loading new containers 22B and 24B in the housing 30B and optionally changing the dispensing tip 150B. In such a procedure, it is desireable to replace each container 22B and 24B with a container of the same substance so there will not be inadvertant premature reactions of components within the piercers 116B and 118B or plenums 124 and 126. One way of helping insure that this occurs is to provide an indexing means (e.g. color code) the carpules 22B and 24B, conveniently by color anodizing the metal caps that retain the septums. These then can be matched up with an indexing means such as a color code on the retainer 129 and/or the housing 30B. When this is done, it is desirable to provide a specific orientation for the retainer 129 on the housing 30B. One way in which the can be conveniently accomplished is to place an optional indexing projection 168 on the housing 30B and a matching keyway 170 on the retainer 129. Alternatively, the replacement containers 22B and 24B and new body 129 may be packaged separately to provide a replacement subassembly.

Referring again to FIG. 14, a cross-section front view of the assembled alternate embodiment of FIG. 13 is illustrated. Optional static mixer 170 and an optional seal 172 are included within the dispensing tip 150B. The seal 172, when present, serves to keep the components of the tissue adhesive and/or sealant separated until the static mixing zone.

The portion of the tip 150B that includes the opening 160B is conveniently fabricated by injection molding of a polymer, with polycarbonate resin considered suitable. For example, the USP Class VI grade polycarbonate commercially available as RX2530-118 from Bayer may be used. The seal element 172 may be molded from a medical grade silicone rubber. The remaining portions of the dispensing tip 150B may be molded from medical grade polypropylene.

Figure 15:
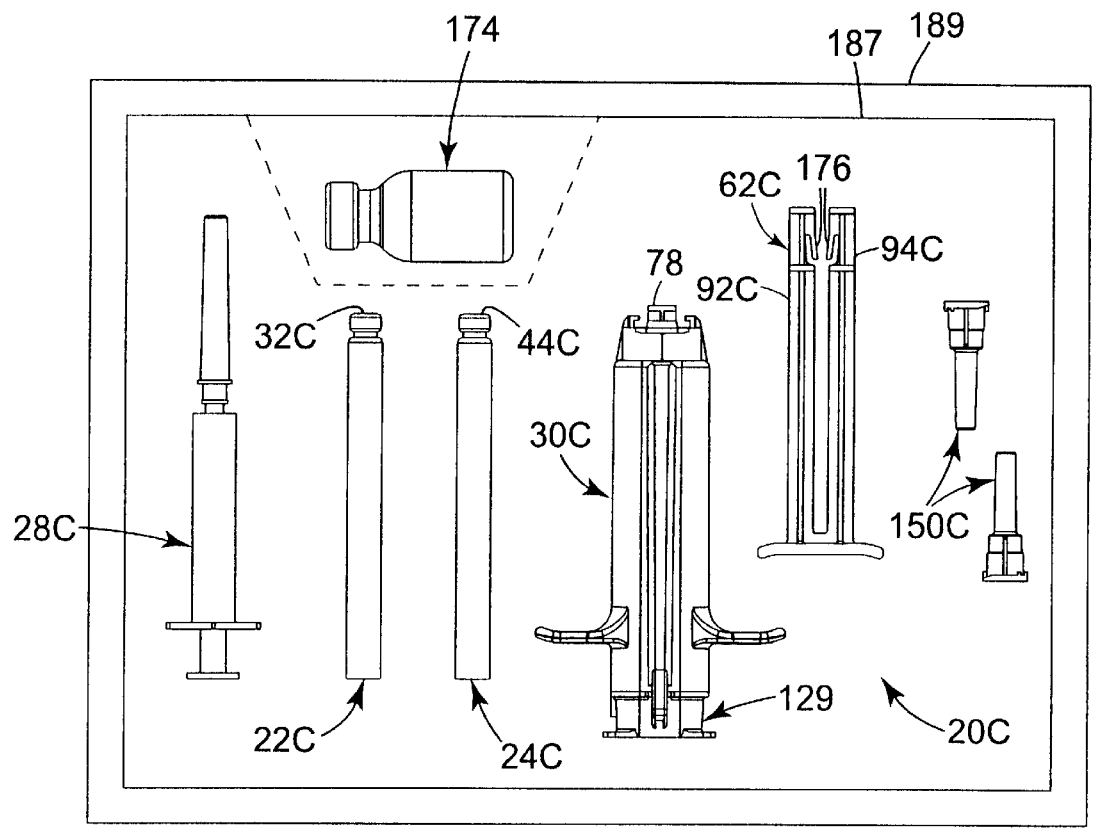
FIG. 15 is a version of a kit including the elements illustrated in FIG. 13.

FIG. 15 illustrates one example of a kit 20C according to the present invention. The kit includes elements useful for preparing and delivering a two component tissue sealant and/or adhesive just prior to use, such as the tissue adhesive/sealant described above with reference to FIGS. 13 and 14.

The kit comprises first container 22C having a septum 32C and at least a portion of a first component of the tissue sealant and/or adhesive (e.g. a dry powder) stored therein, and outer portions that have preferably been sterilized, a second container 24C having at least a portion of the second component (e.g. in the form of a liquid) stored therein and a septum 44C, and outer portions that have preferably been sterilized. When the second component of the tissue adhesive and/or sealant is provided in liquid form, the kit may be free of any solution for reconstituting the second component within the second container 24C.

The kit preferably includes a vial 174 (with inner and outer portions preferably sterile) with a solvent for the dry powder therein. The kit also includes syringe and needle 28C (preferably sterile). The kit also includes dispenser capable of dispensing the tissue sealant and/or adhesive. As best seen in FIG. 14, the dispenser has first and second piercers 116B and 118B located in protected positions and a portion that is sized and shaped to receive the first and second containers.

The components of the kit 20C are packaged within a first package 187. Preferably the inside and outside portions of the elements of the kit 20C are provide in a sterile condition. More preferably, the first package 187 is packaged within a second package 189 and the components within the second package 189 are provided in a sterile condition.

The kit optionally includes one or more dipensing tips 150C and dual piston 62C.

FIGS. 18 through 26 illustrate the use of the kit 20C to deliver a tissue adhesive and/or sealant. If the kit 20C is used to prepare and deliver a tissue adhesive and/or adhesive disclosed in U.S. Pat. No. 5,583,114, then the first and second components may be dispensed without being heated above room temperature. This removes any need to use the kit 20C in conjunction with heating and/or stirring instrumentation. This further simplifies the use of the kit 20C to prepare and deliver a tissue adhesive and/or sealant.

Preferably, the first and second containers 22C and 24C, the dispenser (e.g. 30C), the vial 174 and syringe and needle 28C are provided in sterile condition within first package 187 and the first package 187 is provided in a sterile fashion within a second package 189. In this fashion, the second package 189 may be opened by a healthcare worker outside a sterile area (e.g. a circulating nurse) and the first package 187 may be aseptically taken from the second package 189 and placed in the sterile area by a healthcare worker associated with the sterile area (e.g. a scrub nurse). The first and second packages 187 and 189 may comprise bags (e.g. pouches) or trays or combinations thereof. Trays offer an advantage in that they reduce the number of separate, individual waste products associated with the kit. If the packages 187 or 189 comprise a bag, they are preferably constructed from suitable materials capable of withstanding sterilization processes. For example, such materials include TYVEK and/or MYLAR.

Figure 18:
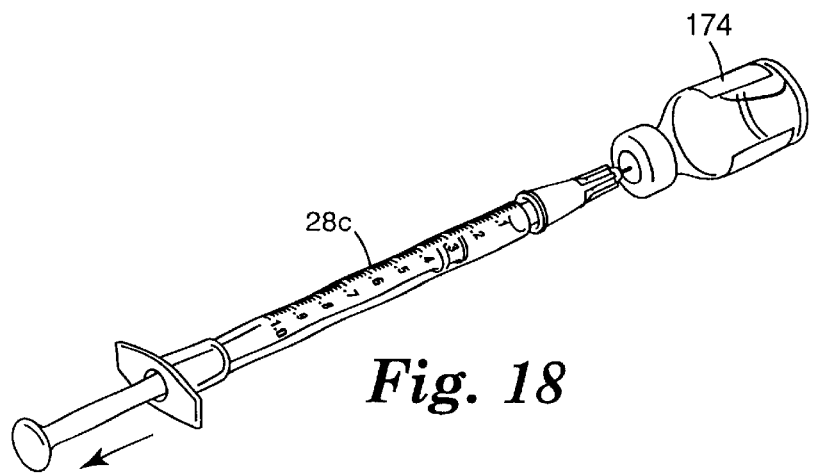
Figure 19:
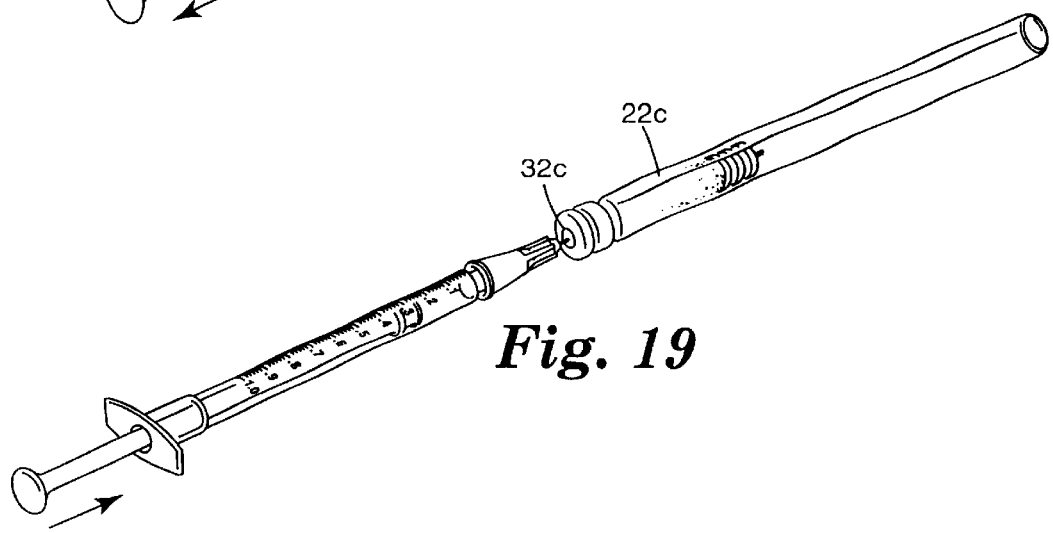

FIG. 18 illustrates the syringe 28C being used to remove the solvent from solvent container 174. The syringe 28C loaded with solvent may then be used to pierce the septum 32C of the container 22C and to inject the solvent for the first component into container 22C. Preferably, the steps shown in FIGS. 18 and 19 are conducted by a single healthcare worker (e.g. a scrub nurse). This removes any need for one healthcare worker to coordinate with another healthcare worker in order to reconstitute any of the components of the tissue adhesive and/or sealant. Alternatively, the solvent may be stored within syringe 28C as the kit is provided (as described above), or the solvent may be stored within the storage bottle 174. This may have the advantage of making the task of sterilizing the total kit for surgical use more convenient.

Figure 20:
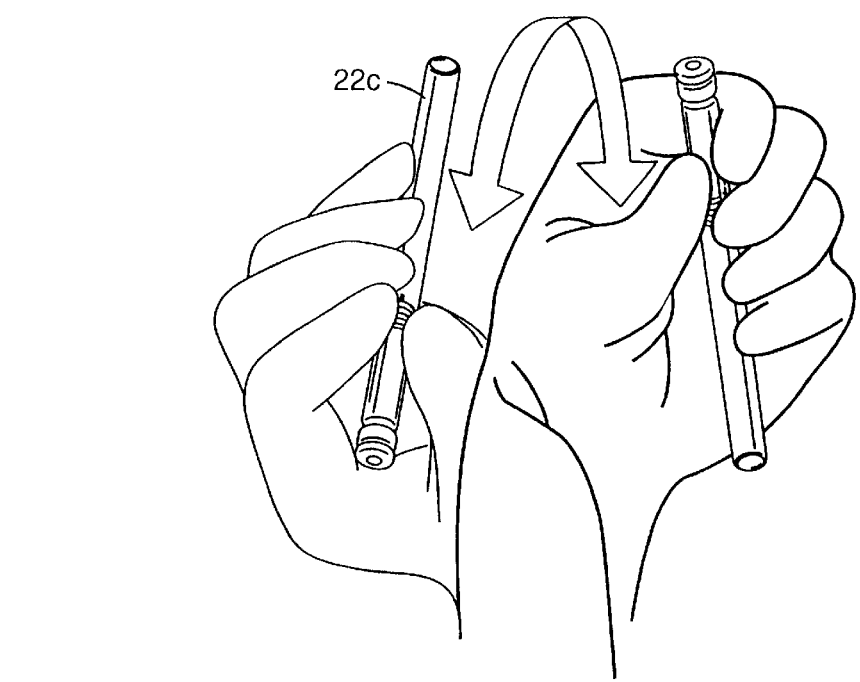

As shown in FIG. 20, the first container 22C is preferably agitated briefly to speed the process of dissolving the first component (e.g. a dry powder) in the solvent.

Figure 21:
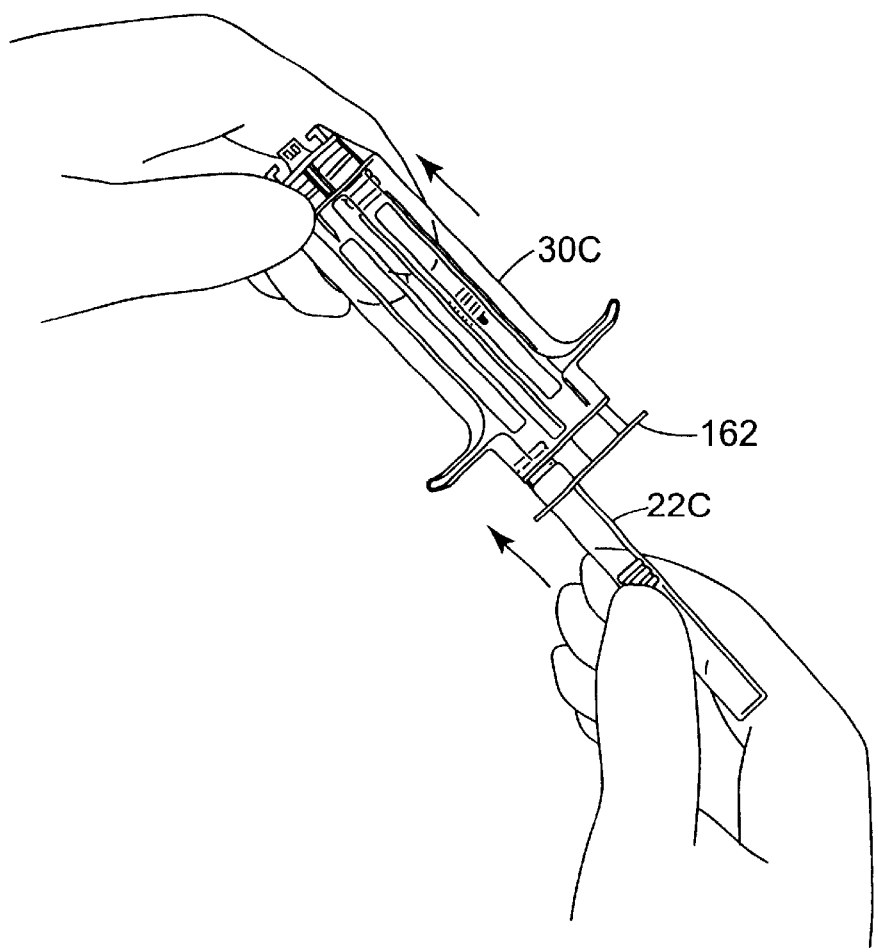

Both containers 22C and 24C may then be inserted though holes in the retainer 129 and impaled on piercers 116B and 118B in the manner shown in FIG. 21. This can be readily conducted by a single healthcare worker without unduly exposing the healthcare worker to the piercers or requiring the healthcare worker to coordinate with another healthcare worker.

Figure 22:
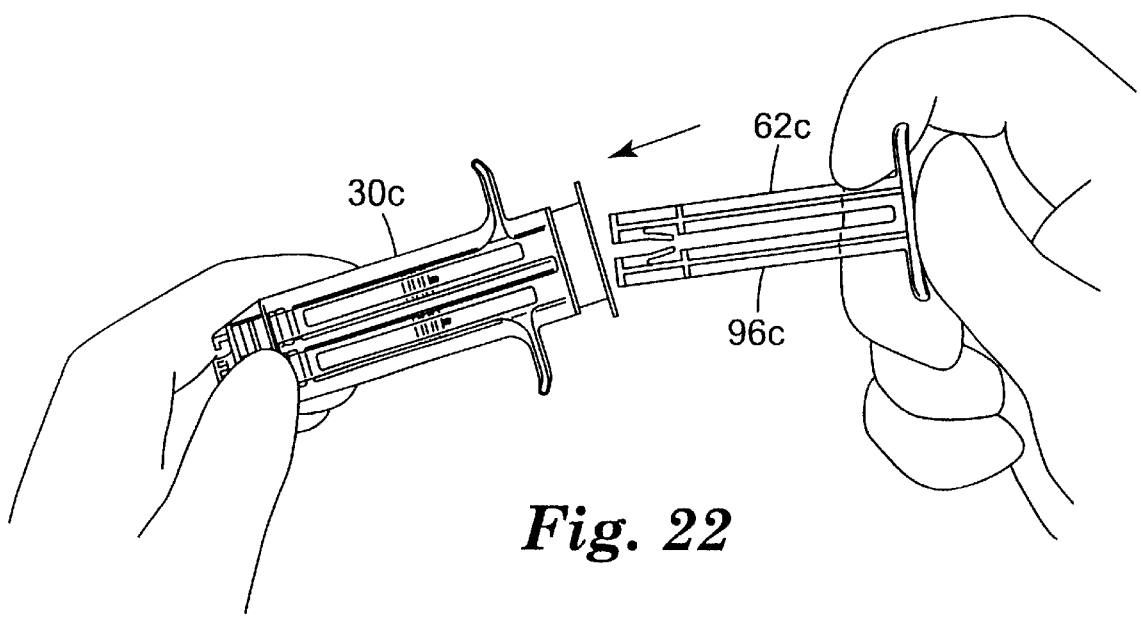

As shown in FIG. 22, dual plunger 62C is inserted into the retainer 129 and on into the distal ends of containers 22C and 24C, lightly touching movable plugs. Spring legs 176 on the dual plunger 62C may conveniently be placed on push rods 92C and 94C to provide a slight friction between the dual plunger 62C and the containers 22C and 24C so as to retain the dual plunger before use.

Figure 23:
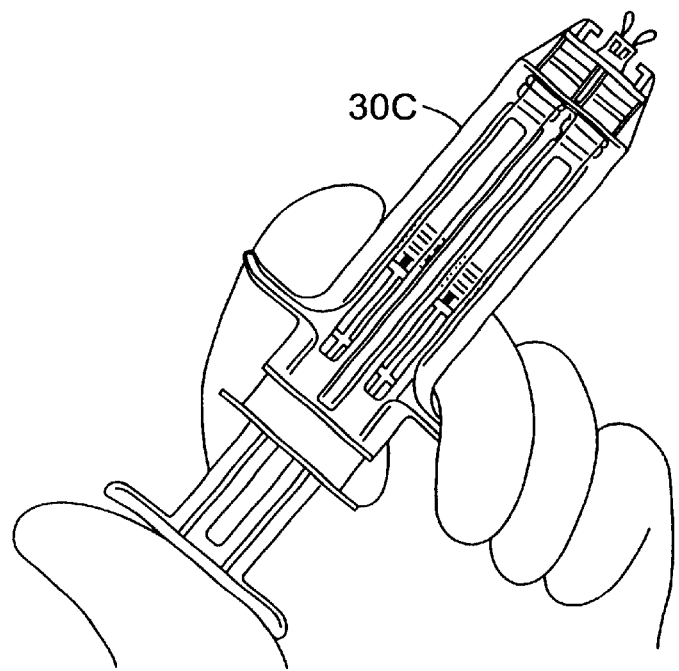
Figure 24:
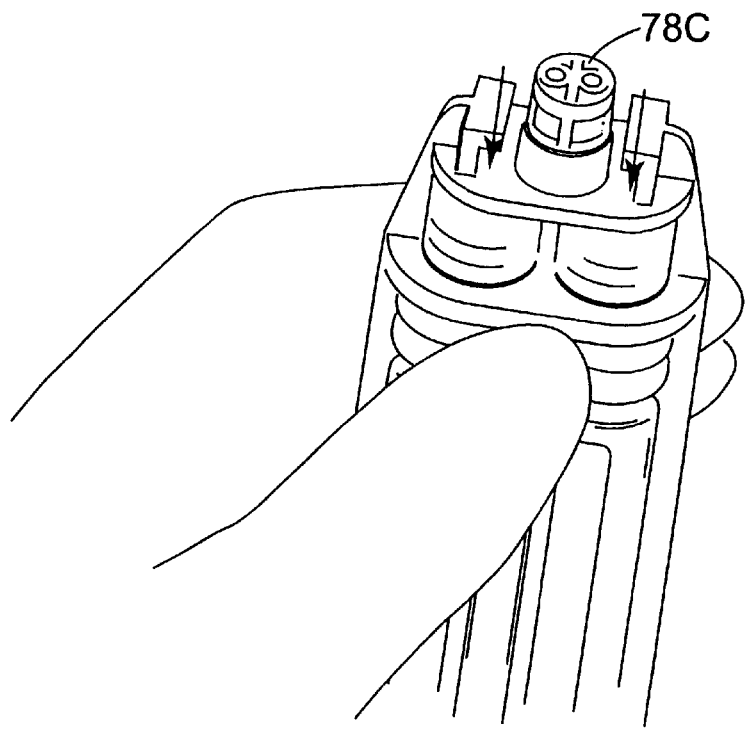

After the syringe 28C adds solution to the container 22C (see FIG. 19), some air remains in the container. As shown in FIG. 23, air is preferably expressed from the assembly. Preferably, after the syringe adds the solution to the powder, the movable member 38B (see FIG. 14 for the member 38B, not its position) is slightly axially offset relative to the movable member 50B so that the dual plunger 62B initially moves the movable member 38B to express the air without moving the movable member 50B. FIG. 14 illustrates the movable members 38B and 50B after the air has been expressed from the first container so that the movable members are substantially axially aligned. In FIG. 24, the distal end (nozzle) of the housing 30C is preferably wiped clean to provide a clean surface for receiving the dispensing tip 150C.

Figure 25:
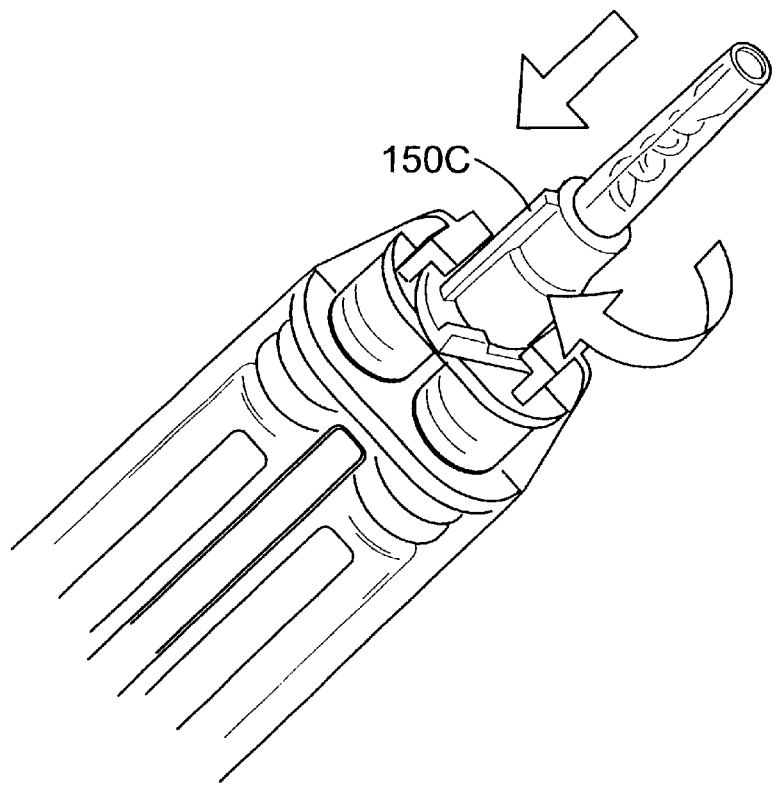

Optionally, but preferably, at least one dispensing tip 150C will be provided, and in some preferred embodiments a second tip will be provided. Placement of the dispensing tip 150C on the housing 30C is shown in FIG. 25. If only a portion of the contents of the containers 22C and 24C is dispensed, and then enough time passes that the mixture within the dispensing tip 150C cross-links or cures sufficient to clog dispensing tip 150C, the second dispensing tip can be attached so that the remain contents of the containers 22C and 24C can be dispensed.

Figure 26:
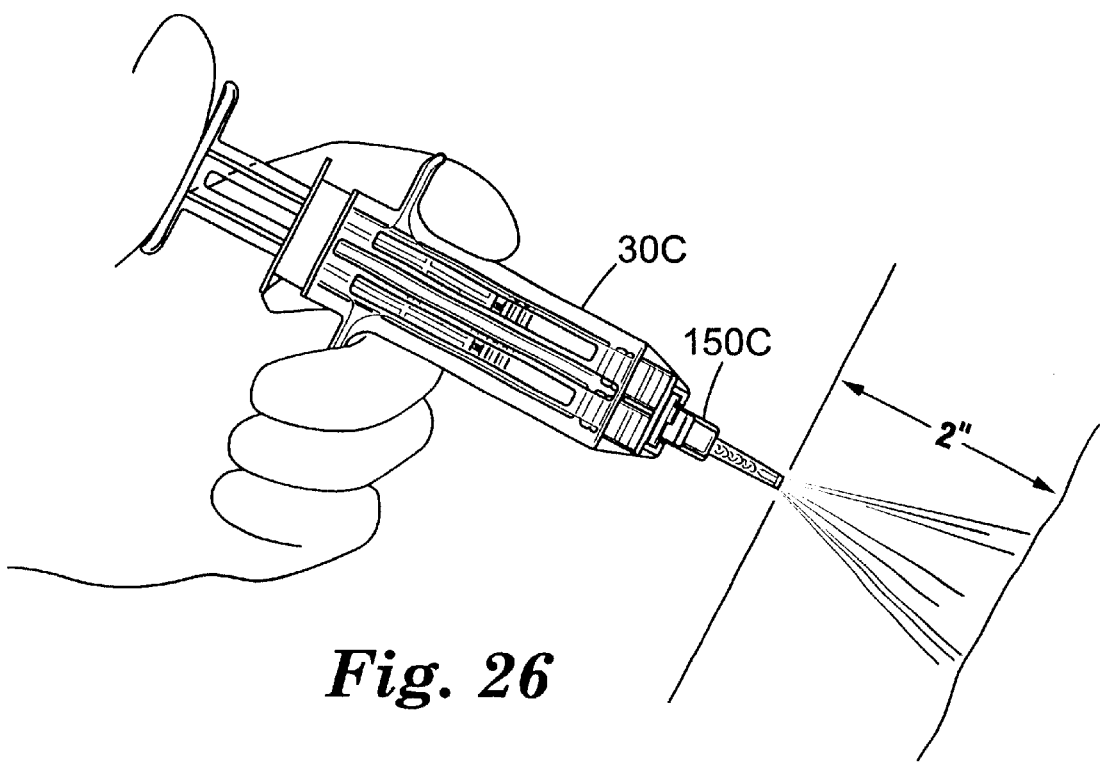

The tissue adhesive and or sealant may then be dispensed or applied as shown in FIG. 26. When the tissue sealant is a tissue sealant constructed according to one embodiment of the teachings of U.S. Pat. No. 5,583,114, "ADHESIVE SEALANT COMPOSITION," then the sealant is preferable dispensed about two inches from the tissue.

In some preferred embodiments, the elements depicted are conveniently packaged together, conveniently all on a single tray formed of e.g. PET, conveniently covered with a cover of e.g. TYVEK spun-bonded polyolefin heat sealed to the tray. If the several elements are most conveniently sterilized for surgical use using different sterilizing techniques, the kit may be provided in two packages, each holding the elements that are expeditiously sterilized together.

It should be noted that all of the steps shown in FIGS. 18–25 may be conducted by a single individual. The step of placing the solvent in the first container (FIG. 18) and the steps of installing the first and second containers in the dispenser (FIG. 22) and piercing the septums of the first and second containers (also FIG. 22) with the first and second piercers are especially convenient when conducted by a single healtcare worker as one healthcare worker need not coordinate activities with another healthcare worker.

Figure 16:
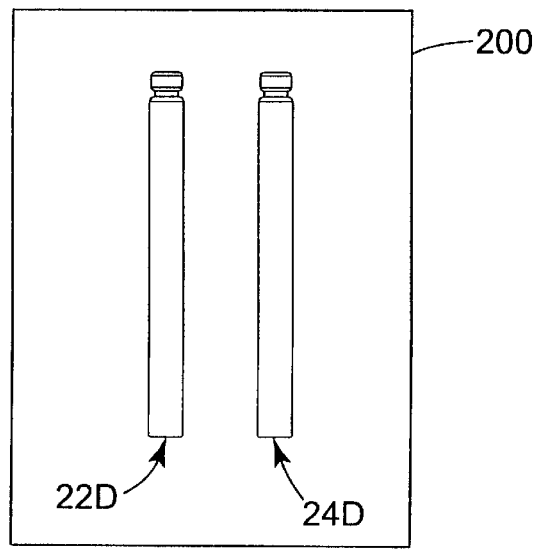
FIG. 16 is a top view of a minor subassembly of a kit according to one aspect of the present invention.
Figure 17:
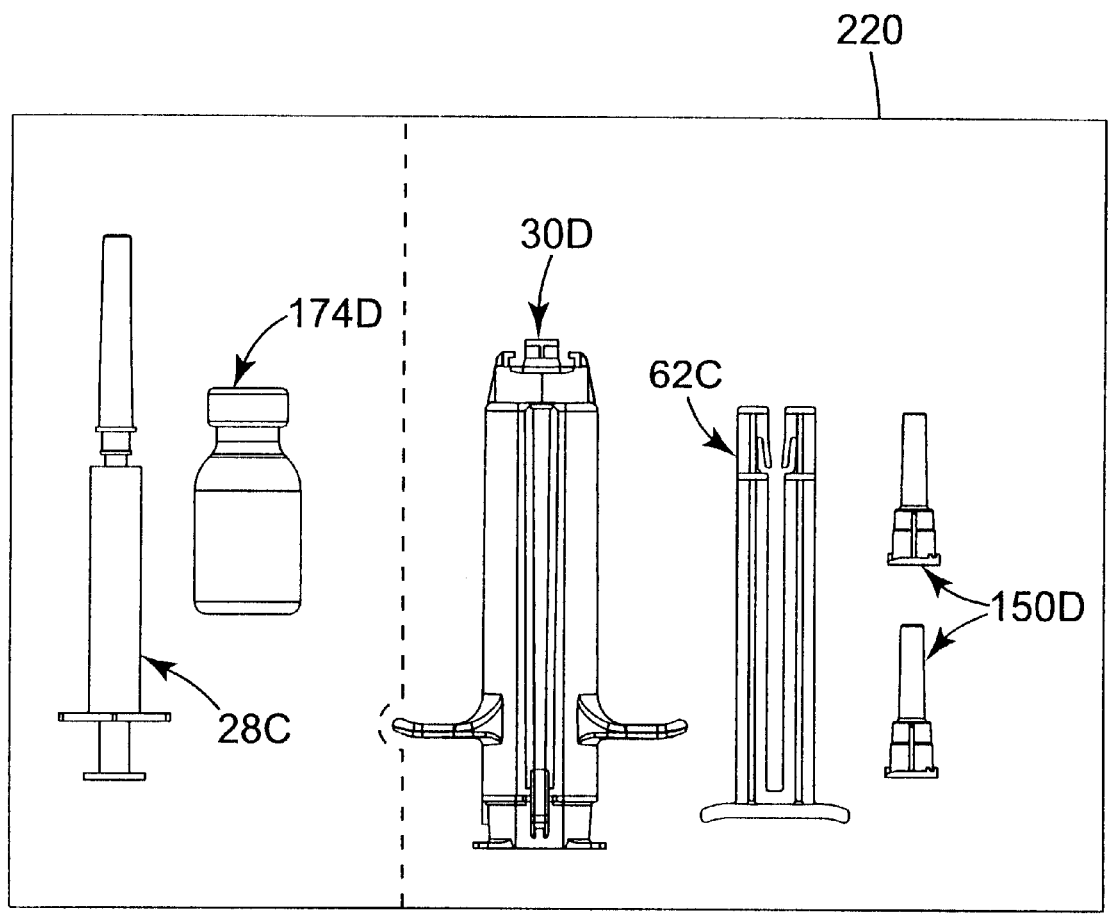
FIG. 17 is a top view of a major subassembly for use with the minor subassembly shown in FIG. 16 according to another aspect of the present invention.

FIGS. 16 and 17 illustrate another embodiment of kit according to the present invention. In FIG. 16, the first and second containers 22C and 24C may be provided in a separate minor subassembly kit 200. Alternatively, the entire preassembly P (See FIG. 11) may be provided in a minor subassembly kit.

FIG. 17 illustrates a major subassembly kit 220 that includes housing 30D, piston 62D, dispensing tips 150D, syringe and needle assembly 28D and solvent (e.g. water) bottle 174D.

The minor subassembly kit 200 may include those elements of the tissue adhesive and/or sealant that include a relatively short shelf life. For example, such labile elements may include a protein solution (e.g. albumin) and dry powder cross-linker component. In another aspect of the present invention, the minor subassembly kit 200 may include those elements of the tissue sealant and/or adhesive that require a different temperature range for storage than the components of the major subassembly kit 220. For example, the minor subassembly kit may include those items that require refrigeration until just prior to use.

In yet another aspect of the invention, the minor subassembly may include those elements of the tissue adhesive and or sealant dispenser that are packaged for a sterilization technique that is different than other portions of the tissue adhesive and or sealant dispenser. For example, the dry powder and liquid components of an adhesive tissue sealant may be sterilized within containers using a low dose e-beam technique (e.g. about 10–20 kGy) and then terminally sterilized using an ethylene oxide sterilization technique. However, the remaining portions of the dispenser need only be subjected to an ethylene oxide sterilization technique. In this embodiment, if the major subassembly includes all of the elements of the kit except containers 22C and 24C, then a majority of the elements of the kit can be sterilized without subjecting them to the effects of the e-beam sterilization technique.

Other embodiments of the invention are within the scope of the following claims. E.g., in some aspects of the invention, materials other than an adhesive tissue sealant may be dispensed, or the solvent for dissolving the dry powder could be nonaqueous. More than two barrels and carpules (e.g., three) could be fitted to a syringe body and manifold. Individual pistons could be used instead of the dual piston. A kit may be sterilized as a whole (e.g. using e-beam or gamma sterilization techniques). Alternatively, individual components may be sterilized, the kit assembled, and then a terminal sterilization of the entire kit could occur.

What is claimed is:

1. A dispenser for simultaneously dispensing first and second components of an adhesive tissue sealant, wherein at least the first component is stored in the dispenser as dry powder that is dissolved prior to use by introduction of a solvent, the dispenser comprising the combination of:

(a) a first container comprising a first septum at one end, an open end opposite the first septum, and a first movable plug disposed therein, the first container containing a quantity of the first component in the form of a dry powder stored between the first septum and the first movable plug;

(b) a second container comprising a second septum at one end, an open end opposite the second septum, and a second movable plug disposed therein, the second container containing a quantity of the second component;

(c) a housing having a pair of cavities sized and configured to receive and support the first and second containers, each cavity having a base, (d) pistons sized and configured to be received in the open ends of the first and second containers to advance the first and second movable plugs; and the housing including a manifold sized and configured to fit over and pierce the first and second septums and to afford passage of the first and second components via first and second flow paths to a nozzle from which the first and second components are dispensed to combine to form the adhesive tissue sealant, first and second piercers mounted in the manifold for piercing the first and second septums, each piercer extending through and being supported by a disk that is supported adjacent the base of said each cavity, each disk being supported a distance spaced from the base of the first and second cavities to form first and second plenums, each plenum defined by said each disk and adjacent walls of said each cavity, the first and second piercers affording passage of the first and second components to the first and second plenums.

2. The dispenser of claim 1 wherein, prior to use, the first movable plug is positioned in a position in which the space between the plug and the septum is substantially the minimum necessary to contain the dry powder, thereby reducing the amount of air in that space.

3. The dispenser of claim 1 wherein the a nozzle is sized and configured so that the first and second components are kept separated until dispensed from the nozzle.

4. The dispenser of claim 1 wherein the second component stored in the second container comprises a liquid.

5. The dispenser of claim 4 wherein the second component is a protein in an aqueous buffer and is capable of reacting with a solution of the first component to provide the adhesive tissue sealant.

6. The dispenser of claim 5 wherein the dry powder forming the first component is a water-compatible or water-soluble cross-linking agent.

7. The dispenser of claim 1 in combination with means for introducing the liquid solvent through the first septum into the first container that is other than the piercers.

8. The dispenser of claim 1 in combination with a syringe sized and configured to inject a liquid solvent into the first container through the first septum.

9. The dispenser of claim 8 wherein the syringe is preloaded with the liquid solvent.

10. The dispenser of claim 8 combined as a kit.

11. The kit of claim 10 wherein the first and second containers are sterile filled and the kit is terminally sterilized.

12. The dispenser of claim 1 wherein the first and second containers are carpules.

13. The dispenser of claim 1 wherein the pistons are connected to form a dual piston.

14. A dispenser for simultaneously dispensing first and second components of a two-part adhesive tissue sealant composition, the dispenser comprising the combination of:

(a) a first container comprising a first septum at one end, an open end opposite the first septum, and a first movable plug disposed therein, the first container containing a quantity of the first component;

(b) a second container comprising a second septum at one end, an open end opposite the second septum, and a second movable plug disposed therein, the second container containing a quantity of the second component, the second component being different from the first component;

(c) a housing sized and configured to receive and support the first and second containers;

(d) pistons sized and configured to enter the open ends of the containers to advance the first and second movable plugs;

the housing including a manifold sized and configured to fit over the first and second septums, the manifold having first and second cavities into which the first and second containers are received, each cavity having a base;

(e) first and second piercers mounted in the manifold for piercing the first and second septums, each piercer extending through and being supported by a disk that is supported adjacent the base of said each cavity, each disk being supported a distance spaced from the base of the first and second cavities to form first and second plenums, each plenum defined by said each disk and adjacent walls of said each cavity, the first and second piercers affording passage of the first and second components to the first and second plenums;

(f) first and second conduits in the manifold that afford passage of the first and second components from the first and second plenums to a nozzle from which the first and second components may be combined to form the adhesive tissue sealant.

15. The dispenser of claim 14 wherein said each disk is sealed to the surrounding wall of said each cavity.

16. The dispenser of claim 15 wherein the seal between the disk and the surrounding wall is provided by an elastomeric seal member on the disk.

17. The dispenser of claim 15 wherein the surronding wall of the cavity is cylindrical and the periphery of the disk is circular.

18. The dispenser of claim 15 wherein one of the first and second conduits and one of the first and second piercers communicate with the corresponding plenum at laterally spaced apart locations so that flow from the piercer lumen to the conduit changes direction from a generally longitudinal flow path through the piercer lumen, to a generally lateral direction in the plenum, and then to a generally longitudinal flow path in the conduit.

19. The dispenser of claim 15 wherein said each disk is supported from the base of said each cavity by standoffs.

20. The dispenser of claim 14 wherein the first container contains a quantity of the first component in the form of a dry powder so that the first component must be dissolved prior to use by introduction of an aqueous solvent and wherein the second component is a protein in an aqueous buffer and the first component is capable of reacting with the second component to provide an adhesive tissue sealant.

21. The dispenser of claim 14 wherein the first and second containers are carpules.

22. The dispenser of claim 14 wherein the first and second containers are sterile filled and the dispenser is terminally sterilized.

23. A dispenser for simultaneously dispensing first and second components of a tissue sealant, wherein at least the first component is stored in the dispenser as dry powder that is dissolved prior to use by introduction of a solvent, the dispenser comprising:

(a) a first container comprising a first septum at one end, an open end opposite the first septum, and a first movable plug disposed therein, the first container containing a quantity of the first component in the form of a dry powder stored between the first septum and the first movable plug; the dry powder being adapted to be dissolved in a solvent just prior to application of the tissue sealant;

(b) a second container comprising a second septum at one end, an open end opposite the second septum, and a second movable plug disposed therein, the second container containing a quantity of the second component;

(c) a housing having internal surfaces with first and second piercers adapted to pierce the first and second septums of the first and second containers, the first and second piercers being situated in protected positions so that the first and second septums may be pierced without exposing a user to contact with the first or second piercers, the housing affording passage of the first and second components via first and second flow paths to a nozzle from which the first and second components are dispensed to combine to form the adhesive tissue sealant, (d) pistons sized and configured to be received in the open ends of the first and second containers to advance the first and second movable plugs; and (e) a body associated with the housing and sized and shaped to receive the first and second containers.

24. A dispenser according to claim 23, wherein the body comprises a retainer that is sized and shaped to protect and support the first and second containers.

25. A dispenser according to claim 24 wherein the retainer includes attachment means for releasably engaging the housing.

26. A dispenser according to claim 25 wherein the retainer includes a distal end that includes the attachment means, and a proximal end having an opening, and the retainer is sized and shaped so that the open ends of the first and second containers do not project beyond the opening of the retainer.

27. A dispenser according to claim 23 wherein the first and second plugs have a lubricant coating to facilitate movement.

28. A dispenser according to claim 27 wherein the lubricant is silicone.

29. A dispenser according to claim 23 wherein the first and second piercers each extend through and are supported by a disk that is supported adjacent the base of a cavity by an O-ring with a lubricant.

30. A dispenser according to claim 29 wherein the lubricant is silicone.

* * * * *

UNITED STATES PATENT AND TRADEMARK OFFICE
CERTIFICATE OF CORRECTION

PATENT NO.    : 6,458,095 B1
DATED         : October 1, 2002
INVENTOR(S)   : David F. Wirt It is certified that error appears in the above-identified patent and that said Letters Patent is hereby corrected as shown below:

Column 5,
Line 11, delete "contant" and insert in place thereof -- contact --;

Column 8,
Line 1, delete the word "of" following "the";

Column 11,
Line 53, delete the word "the" preceding the word "can" and insert in place thereof -- this --;

Column 12,
Line 33, delete the word "provide" and insert in place thereof -- provided --;
Line 37, delete the word "dipensing" and insert in place thereof -- dispensing --;

Column 13,
Line 17, delete the word "though" and insert in place thereof -- through --;
Line 55, delete the word "remain" and insert in place thereof -- remaining --;
Line 61, delete the word "preferable" and insert in place thereof -- preferably --;

Column 14,
Line 12, delete the word "healtcare" and insert in place thereof -- healthcare --;
Line 15, insert -- the -- preceding the word "kit";

Column 15,
Line 38, delete "a nozzle" and insert in place thereof -- nozzle that --;

UNITED STATES PATENT AND TRADEMARK OFFICE
CERTIFICATE OF CORRECTION

PATENT NO. : 6,458,095 B1
DATED : October 1, 2002
INVENTOR(S) : David F. Wirt

It is certified that error appears in the above-identified patent and that said Letters Patent is hereby corrected as shown below:

<u>Column 16,</u>
Line 28, insert -- the -- preceding the word "said";
Line 41, delete "surronding" and insert in place thereof -- surrounding --.

Signed and Sealed this

Twenty-third Day of December, 2003

JAMES E. ROGAN
*Director of the United States Patent and Trademark Office*